US012572623B2

(12) United States Patent
Belloso et al.

(10) Patent No.: US 12,572,623 B2
(45) Date of Patent: Mar. 10, 2026

(54) MACHINE LEARNING FOR INTELLIGENT RADIOTHERAPY DATA ANALYTICS

(71) Applicant: VARIAN MEDICAL SYSTEMS, INC., Palo Alto, CA (US)

(72) Inventors: Jose Carlos Belloso, Madrid (ES); Sven Ehmes, Steinhausen (CH)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1138 days.

(21) Appl. No.: 17/488,198

(22) Filed: Sep. 28, 2021

(65) Prior Publication Data

US 2023/0102914 A1 Mar. 30, 2023

(51) Int. Cl.
| | |
|---|---|
| *G16H 40/60* | (2018.01) |
| *A61N 5/00* | (2006.01) |
| *G06F 16/334* | (2025.01) |
| *G06F 18/21* | (2023.01) |
| *G06N 20/00* | (2019.01) |

(52) U.S. Cl.
CPC ........... *G06F 18/2178* (2023.01); *A61N 5/00* (2013.01); *G06F 16/3344* (2019.01); *G06N 20/00* (2019.01); *G16H 40/60* (2018.01)

(58) Field of Classification Search
CPC ........ G16H 40/40; G16H 40/00; G16H 40/60; G16H 40/63; G06N 20/00; G06F 18/2178; G06F 16/3344; A61N 5/00; A61N 5/1075
See application file for complete search history.

(56) References Cited

U.S. PATENT DOCUMENTS

| | | | |
|---|---|---|---|
| 11,010,233 B1 | 5/2021 | Golden et al. | |
| 2015/0227838 A1* | 8/2015 | Wang | G16H 40/40 |
| | | | 706/12 |
| 2020/0337648 A1* | 10/2020 | Saripalli | G06N 20/00 |
| 2021/0248122 A1* | 8/2021 | Baum | G06F 16/2477 |
| 2022/0088415 A1* | 3/2022 | Winfield | A61N 5/1075 |

FOREIGN PATENT DOCUMENTS

WO WO-2021092845 A1 * 5/2021 ........... A61N 5/1045

OTHER PUBLICATIONS

International Preliminary Report on Patentability for PCT App. PCT/US2022/041175 dated Apr. 2, 2024 (7 pages).
International Search Report and Written Opinion on PCT Appl. Ser. No. PCT/US2022/041175 dated Dec. 5, 2022 (13 pages).

* cited by examiner

*Primary Examiner* — Daniel T Pellett
(74) *Attorney, Agent, or Firm* — Foley & Lardner LLP

(57) ABSTRACT

Disclosed herein are systems and methods for predicting performance attributes of radiotherapy machines. A processor generates a machine-readable object by executing an algorithm using an electronic log file comprising at least one operational attribute of a radiotherapy machine and a corresponding timestamp. The processor executes a machine learning model using the machine-readable object to predict a performance attribute of the radiotherapy machine. The processor provides the predicted performance attribute of the radiotherapy machine to an electronic device.

20 Claims, 24 Drawing Sheets

200b 0513 0.0001</NOMINALIONCHARGER f><NOMINALIONCHARGEG MIN="1e-05" MAX="0.001">0.0001</NOMINALIONCHARGEH MIN="1e-05" MAX="0.001">0.0001</NOM
0514 0</SYMMETRYPT></BEAMSTEERING><STATICCOILCURRENT><BUNCHER MIN="3" MAX="3">0</BUNCHER><BUNCHERT MIN="3" MAX="3">0</BUNCHERT><TRIM MIN="3" MAX="3">
0515 0<BEAMERBMAGROFFSET MIN="0" MAX="0.07">0.001</BEAMERBMAGILIMIT MIN="0" MAX="98">90</BEAMERBMAGILIMIT></SATURATIONCURRENT></SOLENOID
0516 1</GAIN><OFFSET MIN="0" MAX="0">0</OFFSET></SECONDARYDOSIMETRY><ARSYMMETRY><GAIN MIN="-20" MAX="20">-1</GAIN><BALANCEGAIN MIN="1" MAX="1">-1</BALANCEG
0517 0</OFFSET></AFCERROR><BEAMHOLDERSERVOFACTOR>-1</BEAMHOLDERSERVOFACTOR></AFCSENSOR><SERVOPARAMETERS><DOSESERVO><NUMBEROFPULSES MIN="1" MAX="1">1</NUMBEROFP
0518 0</MAXOUTPUT></STEERSERVO><OUTPUTRATELIMIT MIN="0" MAX="0">0</OUTPUTRATELIMIT></STEERSERVO><AFCSERVO><OUTPUTRATELIMIT MIN="0" MAX="0">0</o
0519 0</PCNT25 COUNT="0"><MINCOUNT>72000</MINCOUNT></PCNT25></PCNT50 COUNT="0"><MINCOUNT>72000</MINCOUNT></PCNT50></PCNT75 COUNT="0"><MINCOUNT>72000</MINCO
0520 0</STABLEVAL></BEAMRESUMESTATS></PFNSERVO></CONTROLLIMIT><DOSERATETABLE><DOSERATEMUPERMIN="0"><MINCOUNT>120</MINCOUNT><MODRATE><NUMPULSEDROP
0521 1</NOMINALIONCHARGEG MIN="2.5" MAX="2.5"><SYMMETRYPT></BEAMSTEERING><STATICCOILCURRENT><BUNCHER MIN="3" MAX="3">-0.015</BUNCHER><BUNCHERT MIN="3"
0522 <SYMMETRYPT MIN="-2.5" MAX="2.5">-0.468</SYMMETRYPT></BEAMERBMAGROFFSET MIN="0" MAX="0.05">0.05">0.174303</NOMINALIONCHARGEH></NOMINALIONCH
0523 <BEAMERBMAGIOFFSET MIN="0" MAX="2.50">90</BEAMERBMAGILIMIT></PRIMARYDOSIMETRY><GAIN MIN="0.001" MAX="0.1">0.011244</GAIN><OFFSET MIN="-10" MAX="10">0</OFFSET></PRIMARYDOSIMETRY>X
0524 </BEAMER><DOSIMETRYCALIBPARAM><PRIMARYDOSIMETRY><SENSITIVITY></PFNSERVO></BEAMSTEERING><STATICCOILCURRENT><BUNCHER MIN="3" MAX="3">-0.015</BUNCHER><BUNCHERT MIN="3"
0525 <FLATNESS><BALANCEGAIN MIN="0.001" MAX="15">-8.61665</BALANCEGAIN><TOTALGAIN MIN="1" MAX="10">5</TOTALGAIN></FLATNESS><TARGETCURRENT></GAIN MIN="-10"
0526 8</NUMBEROFPULSES></SENSITIVITY MIN="0.001" MAX="10">0.09</SENSITIVITY></PREAMSTEERING><NUMBEROFPULSES><NUMBEROFPULSES MIN="1" MAX="50">6</NUMBEROFPU
0527 0.1</MAXSTEPSIZE><DELAYCOUNT MIN="0" MAX="100">30</DELAYCOUNT></BEAMPULSEDELAY MIN="0" MAX="100">10</BEAMPULSEDELAY><NOMINALFACTOR MIN="0.01" MAX="2">
0528 <MINCOUNT>72000</MINCOUNT></TRANSMIN><STABLECNT COUNT="8" MIN="1" MAX="18A" AVG="68.1667" LAST="1"><MINCOUNT>72000</MINCOUNT><STABLEVAL><STABLEVAL
0529 <MINCOUNT>72000</MINCOUNT></STABLECNT><STABLEVAL COUNT="537" MIN="0.90845" MAX="1.02659" AVG="0.9727" LAST="0.946772" LAST="1.02059</MINCOUNT>/MINCOUNT></
0530 <GUNPULSEWIDTH MIN="0" MAX="1">1</GUNPULSEWIDTH></DOSERATE><DOSERATE MUPERMIN="60"><MODRATE MUPERMIN="60"><MODRATE><NUMPULSEDROP MIN="0" MA
0531 0</NUMPULSEDROP><GUNPULSEWIDTH MIN="0" MAX="1">1</GUNPULSEWIDTH></DOSERATE><DOSERATE MUPERMIN="300"><MODRATE MIN="120" MAX="400">180</MODRATE><NUMPUL
0532 <NOMINALIONCHARGED MIN="1.2" MAX="4.5">2.55957</NOMINALIONCHARGED><NOMINALIONCHARGEE><NOMINALIONCHARGE MIN="0.5">0.381046</NOMINALIONCHAR
0533 -7500</HIGHVOLTAGE></GUNDRIVER><BEAMSTEERING><SYMMETRYAR MIN="1" MAX="1">0.07</SYMMETRYAR><SYMMETRYAT MIN="1" MAX="1">0.036</SYMMETRYAT></SYMMETRYPR

FIG. 2B

Figure 4D:
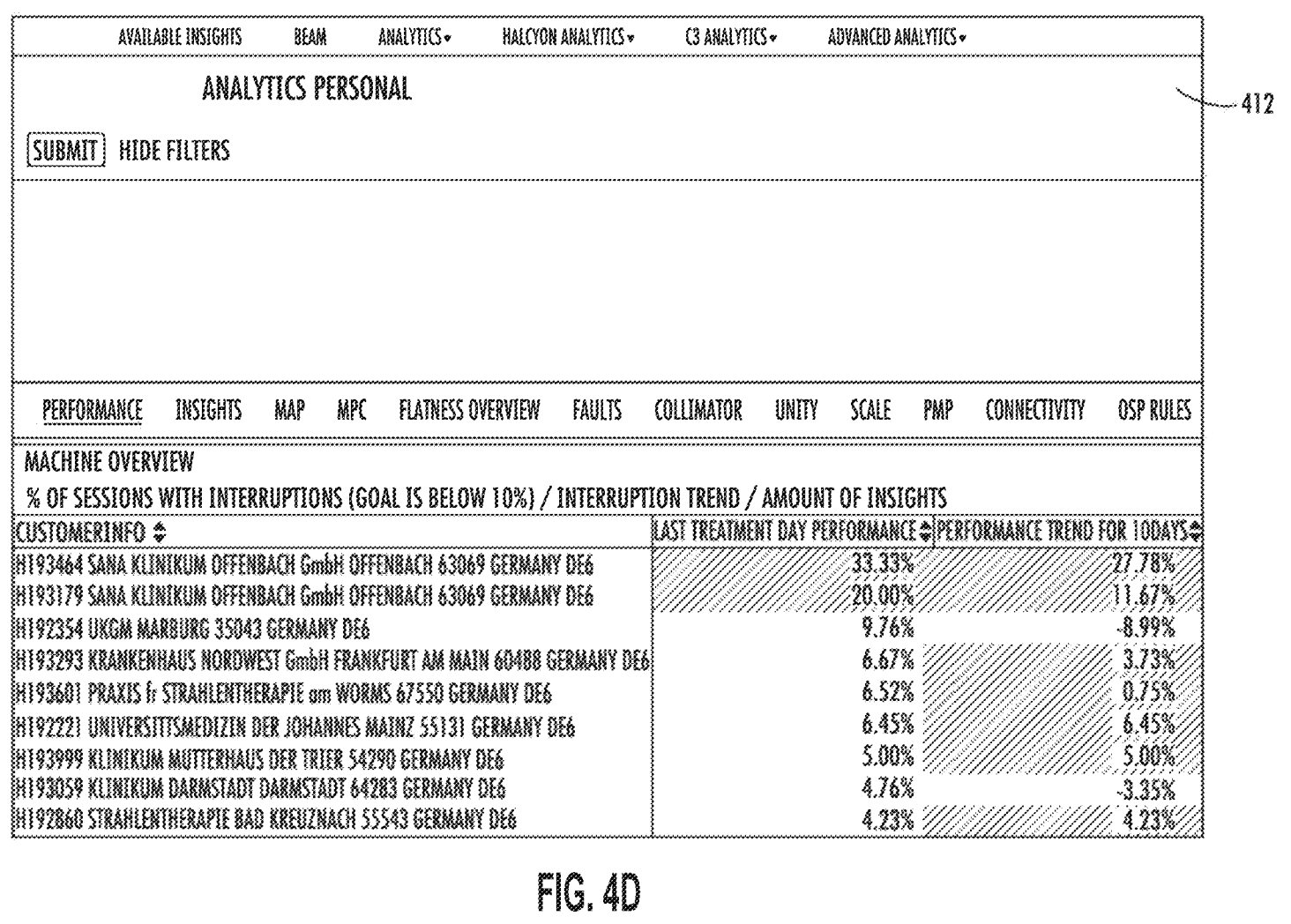

AVAILABLE INSIGHTS   BEAM   ANALYTICS▼   HALCYON ANALYTICS▼   C3 ANALYTICS▼   ADVANCED ANALYTICS▼

ANALYTICS PERSONAL

[SUBMIT] HIDE FILTERS

412

PERFORMANCE   INSIGHTS   MAP   MPC   FLATNESS OVERVIEW   FAULTS   COLLIMATOR   UNITY   SCALE   PMP   CONNECTIVITY   QSP RULES

MACHINE OVERVIEW

% OF SESSIONS WITH INTERRUPTIONS (GOAL IS BELOW 10%) / INTERRUPTION TREND / AMOUNT OF INSIGHTS

| CUSTOMERINFO ⬍ | LAST TREATMENT DAY PERFORMANCE ⬍ | PERFORMANCE TREND FOR 10 DAYS ⬍ |
|---|---|---|
| H193464 SANA KLINIKUM OFFENBACH GmbH OFFENBACH 63069 GERMANY DE6 | 33.33% | 27.78% |
| HF83179 SANA KLINIKUM OFFENBACH GmbH OFFENBACH 63069 GERMANY DE6 | 20.00% | 11.67% |
| H192354 UKGM MARBURG 35043 GERMANY DE6 | 9.76% | -8.99% |
| H192293 KRANKENHAUS NORDWEST GmbH FRANKFURT AM MAIN 60488 GERMANY DE6 | 6.67% | 3.73% |
| H193601 PRAXIS Fr STRAHLENTHERAPIE am WORMS 67550 GERMANY DE6 | 6.52% | 0.75% |
| H192221 UNIVERSITTSMEDIZIN DER JOHANNES MAINZ 55131 GERMANY DE6 | 6.45% | 6.45% |
| H193999 KLINIKUM MUTTERHAUS DER TRIER 54290 GERMANY DE6 | 5.00% | 5.00% |
| H198059 KLINIKUM DARMSTADT DARMSTADT 64283 GERMANY DE6 | 4.76% | -3.35% |
| H192860 STRAHLENTHERAPIE BAD KREUZNACH 55543 GERMANY DE6 | 4.23% | 4.23% |

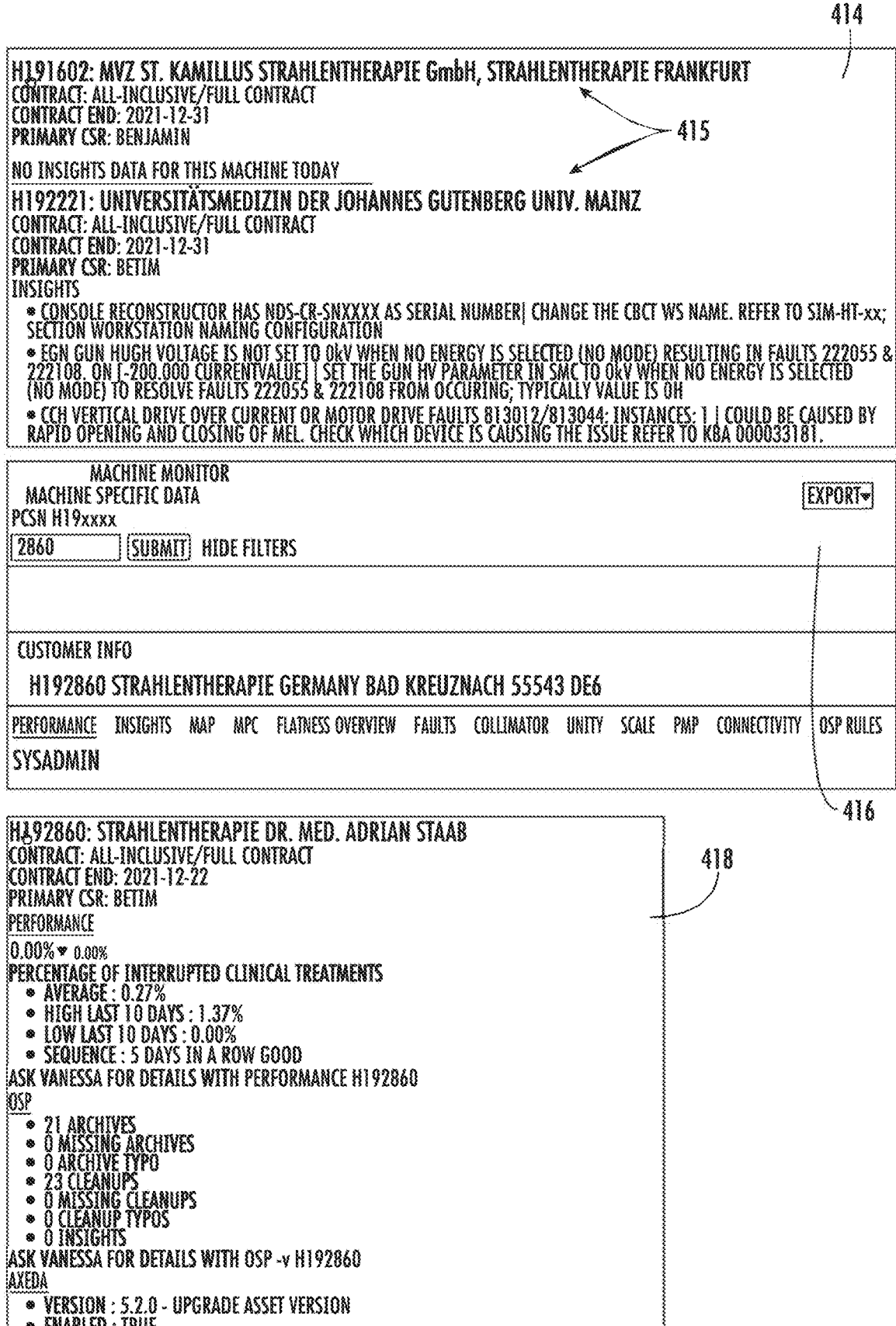

H191602: MVZ ST. KAMILLUS STRAHLENTHERAPIE GmbH, STRAHLENTHERAPIE FRANKFURT
CONTRACT: ALL-INCLUSIVE/FULL CONTRACT
CONTRACT END: 2021-12-31
PRIMARY CSR: BENJAMIN

NO INSIGHTS DATA FOR THIS MACHINE TODAY

H192221: UNIVERSITÄTSMEDIZIN DER JOHANNES GUTENBERG UNIV. MAINZ
CONTRACT: ALL-INCLUSIVE/FULL CONTRACT
CONTRACT END: 2021-12-31
PRIMARY CSR: BETIM
INSIGHTS
   • CONSOLE RECONSTRUCTOR HAS NDS-CR-SNXXXX AS SERIAL NUMBER| CHANGE THE CBCT WS NAME. REFER TO SIM-HT-xx; SECTION WORKSTATION NAMING CONFIGURATION
   • EGN GUN HUGH VOLTAGE IS NOT SET TO 0kV WHEN NO ENERGY IS SELECTED (NO MODE) RESULTING IN FAULTS 222055 & 222108. ON [-200.000 CURRENTVALUE] | SET THE GUN HV PARAMETER IN SMC TO 0kV WHEN NO ENERGY IS SELECTED (NO MODE) TO RESOLVE FAULTS 222055 & 222108 FROM OCCURING; TYPICALLY VALUE IS 0H
   • CCH VERTICAL DRIVE OVER CURRENT OR MOTOR DRIVE FAULTS 813012/813044: INSTANCES: 1 | COULD BE CAUSED BY RAPID OPENING AND CLOSING OF MEL. CHECK WHICH DEVICE IS CAUSING THE ISSUE REFER TO KBA 000033181.

415

MACHINE MONITOR
MACHINE SPECIFIC DATA
PCSN H19xxxx             [EXPORT▾]

[2860]  [SUBMIT]  HIDE FILTERS

CUSTOMER INFO

H192860 STRAHLENTHERAPIE GERMANY BAD KREUZNACH 55543 DE6

PERFORMANCE   INSIGHTS   MAP   MPC   FLATNESS OVERVIEW   FAULTS   COLLIMATOR   UNITY   SCALE   PMP   CONNECTIVITY   | OSP RULES
SYSADMIN

416

H192860: STRAHLENTHERAPIE DR. MED. ADRIAN STAAB
CONTRACT: ALL-INCLUSIVE/FULL CONTRACT
CONTRACT END: 2021-12-22
PRIMARY CSR: BETIM
PERFORMANCE
0.00% ▾ 0.00%
PERCENTAGE OF INTERRUPTED CLINICAL TREATMENTS
   • AVERAGE : 0.27%
   • HIGH LAST 10 DAYS : 1.37%
   • LOW LAST 10 DAYS : 0.00%
   • SEQUENCE : 5 DAYS IN A ROW GOOD
ASK VANESSA FOR DETAILS WITH PERFORMANCE H192860
OSP
   • 21 ARCHIVES
   • 0 MISSING ARCHIVES
   • 0 ARCHIVE TYPO
   • 23 CLEANUPS
   • 0 MISSING CLEANUPS
   • 0 CLEANUP TYPOS
   • 0 INSIGHTS
ASK VANESSA FOR DETAILS WITH OSP -v H192860
AXEDA
   • VERSION : 5.2.0 - UPGRADE ASSET VERSION
   • ENABLED : TRUE
   • CONNECTED : TRUE

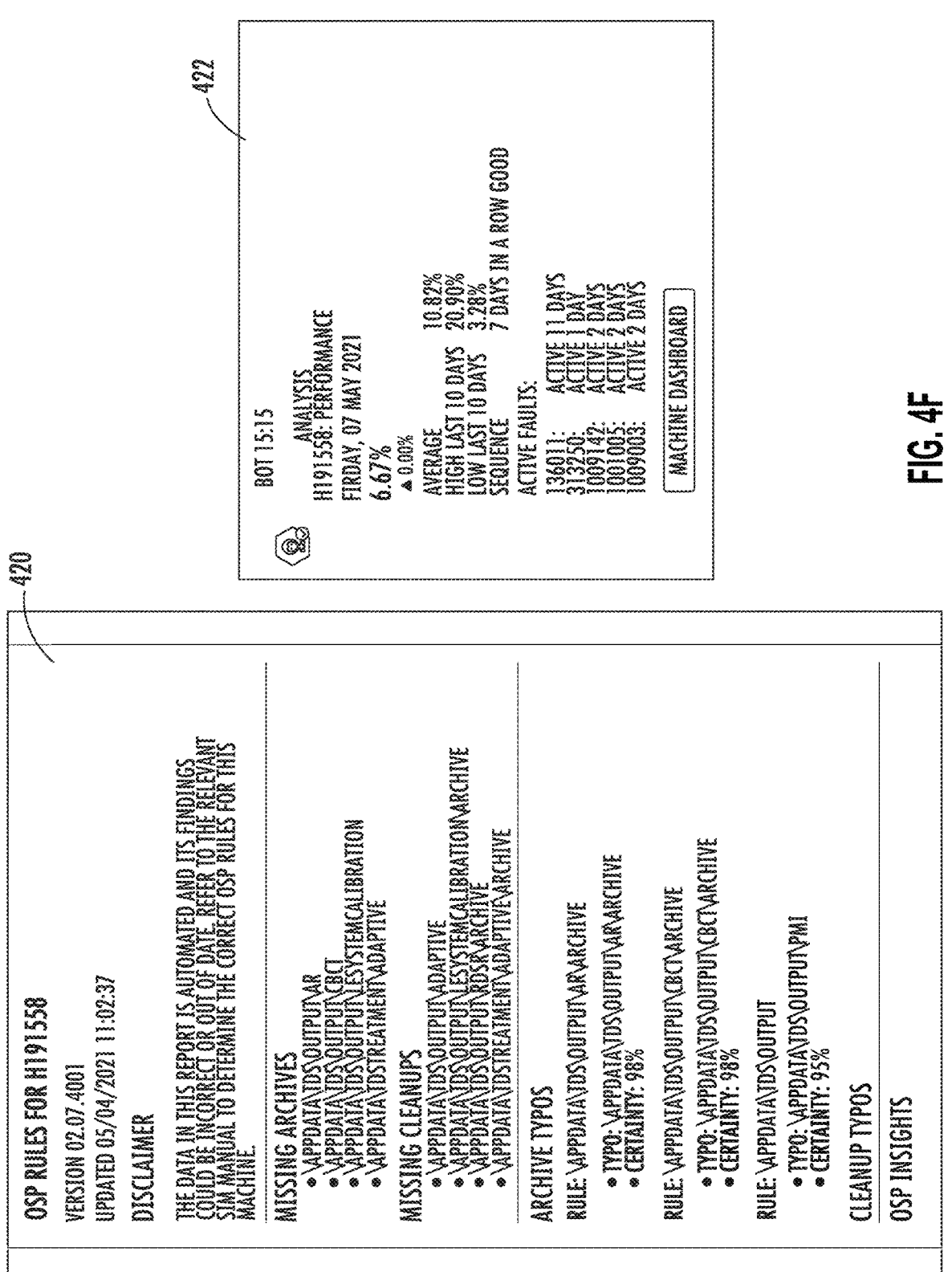

OSP RULES FOR H191558

VERSION 02.07.4001

UPDATED 05/04/2021 11:02:37

DISCLAIMER

THE DATA IN THIS REPORT IS AUTOMATED AND ITS FINDINGS COULD BE INCORRECT OR OUT OF DATE. REFER TO THE RELEVANT SIM MANUAL TO DETERMINE THE CORRECT OSP RULES FOR THIS MACHINE.

MISSING ARCHIVES
- \APPDATA\TDS\OUTPUT\AR
- \APPDATA\TDS\OUTPUT\CBCT
- \APPDATA\TDS\OUTPUT\LESYSTEMCALIBRATION
- \APPDATA\TDS\TREATMENT\ADAPTIVE

MISSING CLEANUPS
- \APPDATA\TDS\OUTPUT\ADAPTIVE
- \APPDATA\TDS\OUTPUT\LESYSTEMCALIBRATION\ARCHIVE
- \APPDATA\TDS\OUTPUT\RDSR\ARCHIVE
- \APPDATA\TDS\TREATMENT\ADAPTIVE\ARCHIVE

ARCHIVE TYPOS

RULE: \APPDATA\TDS\OUTPUT\AR\ARCHIVE
- TYPO: \APPDATA\TDS\OUTPUT\AR\ARCHIVE
- CERTAINTY: 98%

RULE: \APPDATA\TDS\OUTPUT\CBCT\ARCHIVE
- TYPO: \APPDATA\TDS\OUTPUT\CBCT\ARCHIVE
- CERTAINTY: 98%

RULE: \APPDATA\TDS\OUTPUT
- TYPO: \APPDATA\TDS\OUTPUT\PMI
- CERTAINTY: 95%

CLEANUP TYPOS

OSP INSIGHTS

---

BOT 15:15

ANALYSIS
H191558: PERFORMANCE

FIRDAY, 07 MAY 2021

6.67%
▲ 0.00%

AVERAGE 10.82%
HIGH LAST 10 DAYS 20.90%
LOW LAST 10 DAYS 3.28%
SEQUENCE 7 DAYS IN A ROW GOOD

ACTIVE FAULTS:

136011: ACTIVE 11 DAYS
313250: ACTIVE 1 DAY
1009142: ACTIVE 2 DAYS
1001005: ACTIVE 2 DAYS
1089003: ACTIVE 2 DAYS

[MACHINE DASHBOARD]

AVAILABLE HIGH PRIORITY INSIGHTS

| | INSIGHT ⬦ | SUGGESTED ACTION ⬦ |
|---|---|---|
| 1 | MLC SOFPOT | B60 SOFTPOT ISSUE; CONSIDER REPLACING THE SOFTPOT [LEAVES]: B60 |
| 2 | MLC CONTROLLER HAS UNUSUAL AMOUNT OF INITIALIZATIONS. [GOOD: 12; BAD:0] CALIBRATIONS [GOOD:0; BAD:0] | GO TO VIDA DASHBOARD FOR ADDITIONAL INFO |
| 3 | THE NTP TIME SERVER IS NOT CONFIGURED OR PROPERLY SETUP RESULTING IN TIME SYNC ERRORS. 4 TIMES | CONFIGURE AND/OR VERIFY THE NTP TIME SERVER IS PROPERLY SETUP. REFER TO SIM-HT-02x ... |
| 4 | BAD PERFORMANCE 40.48% OF INTERRUPTED SESSIONS. 313253 ARE 28.57%. 420208 ARE 28.57% | GO TO VIDA DASHBOARD FOR ADDITIONAL INFO |
| 5 | CTRL CONS FAULT 313253; DKB GPIO & CLPD SIGNAL MISMATCH. [10 INSTANCES] | THIS IS TYPICALLY AN ISSUE INSIDE THE DKB WITH INTERNAL TIMING. CONSIDER REPLACEMENT OF THE DKB. PN: 100035767. REFER TO PFU-108 "TRUEBEAM CONTROL CONSOLE FRUs" |

AVAILABLE LOW PRIORITY INSIGHTS

| | INSIGHT ⬦ | SUGGESTED ACTION ⬦ |
|---|---|---|
| 1 | BGM GUN DURATION IS SET OUTSIDE TYPICAL VALUES. 6x [4.080 CURRENTVALUE] | REFER TO THE CAL-HT-DSxx; SECTION "TUNING BEAM AND DOSE RATE" FOR PROPER SETTING.; TYPICALLY VALUE ARE BETWEEN 5.2 AND 4.2 |
| 2 | BGM POS HOME SWITCH TOO CLOSE TO HARD STOP FOR YAXIS [0.447 CURRENTVALUE] | ADJUST THE HOME SWITCH TO AVOID POSSIBLE MECHANICAL DAMAGE. REFER TO CAL-HT-DS02 LS: SECTION "VERIFY AXIS LIMIT SWITCH POSITION" FOR LIMIT SWITCH SPECIFICATIONS.; TYPICALLY VALUE ARE BETWEEN 1.2 AND 0.5 |
| 3 | BGM POS HOME SWITCH TOO CLOSE TO HARD STOP FOR ENSW [0.661 CURRENTVALUE] | ADJUST THE HOME SWITCH TO AVOID POSSIBLE MECHANICAL DAMAGE. REFER TO CAL-HT-DS02 LS: SECTION "VERIFY AXIS LIMIT SWITCH POSITION" FOR LIMIT SWITCH SPECIFICATIONS.; TYPICALLY VALUE ARE BETWEEN 9.2 AND 0.9 |

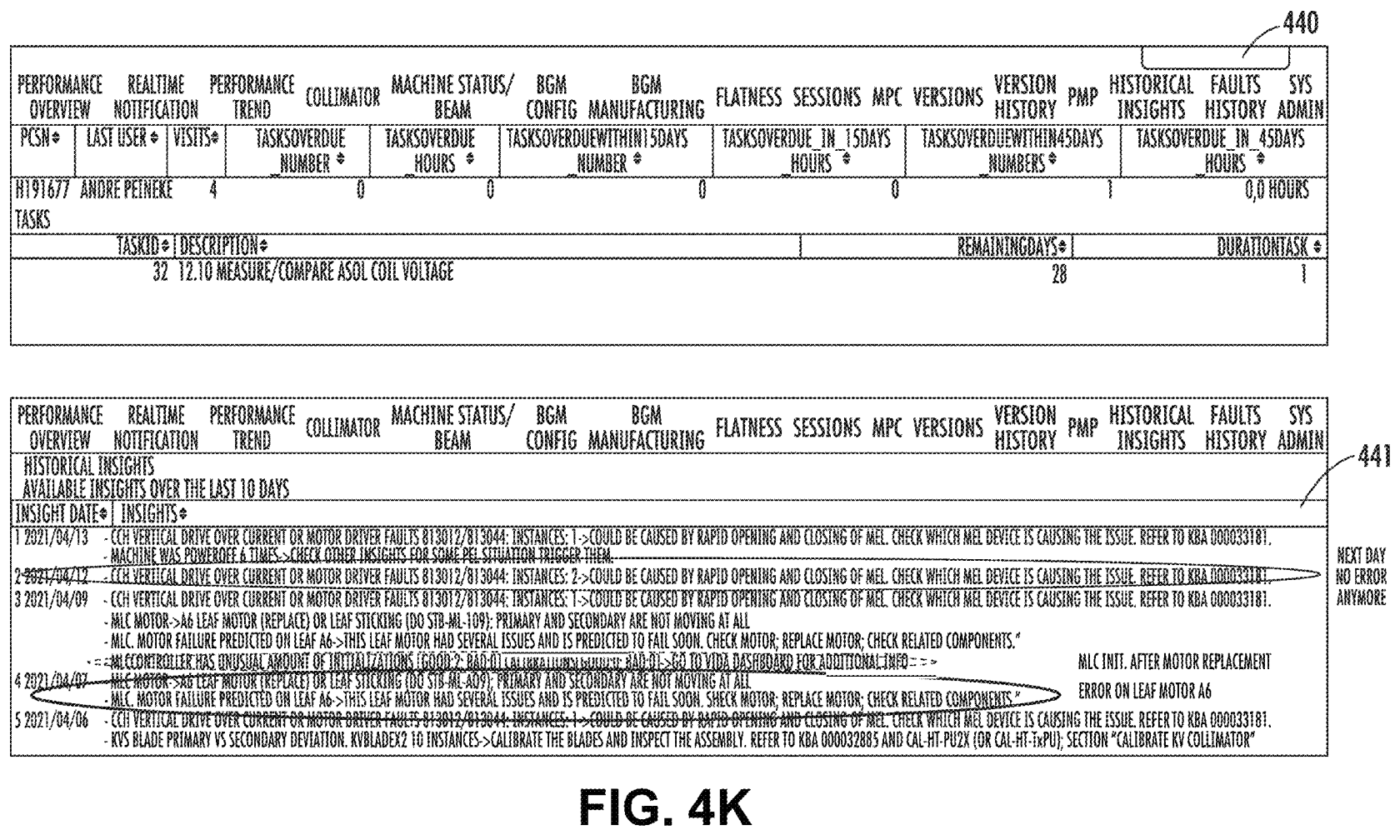

| PERFORMANCE OVERVIEW | REALTIME NOTIFICATION | PERFORMANCE TREND | COLLIMATOR | MACHINE STATUS/ BEAM | BGM CONFIG | BGM MANUFACTURING | FLATNESS | SESSIONS | MPC VERSIONS | VERSIONS HISTORY | PMP HISTORY | HISTORICAL INSIGHTS | FAULTS HISTORY | SYS ADMIN |

| PCSN ◆ | LAST USER ◆ | VISITS ◆ | TASKSOVERDUE NUMBER ◆ | TASKSOVERDUE HOURS ◆ | TASKSOVERDUEWITHIN 5DAYS NUMBER ◆ | TASKSOVERDUE IN 5DAYS HOURS ◆ | TASKSOVERDUEWITHIN45DAYS NUMBERS ◆ | TASKSOVERDUE IN 45DAYS HOURS ◆ |
|---|---|---|---|---|---|---|---|---|
| H19 1677 | ANDRE PEINEKE | 4 | 0 | 0 | 0 | 0 | 1 | 0.0 HOURS |

TASKS

| TASKID ◆ | DESCRIPTION ◆ | REMAININGDAYS ◆ | DURATIONTASK ◆ |
|---|---|---|---|
| 32 | 12.10 MEASURE/COMPARE ASOL COIL VOLTAGE | 28 | 1 |

441

| PERFORMANCE OVERVIEW | REALTIME NOTIFICATION | PERFORMANCE TREND | COLLIMATOR | MACHINE STATUS/ BEAM | BGM CONFIG | BGM MANUFACTURING | FLATNESS | SESSIONS | MPC VERSIONS | VERSIONS HISTORY | PMP HISTORY | HISTORICAL INSIGHTS | FAULTS HISTORY | SYS ADMIN |

HISTORICAL INSIGHTS
AVAILABLE INSIGHTS OVER THE LAST 10 DAYS

| INSIGHT DATE ◆ | INSIGHTS ◆ |
|---|---|
| 1 2021/04/13 | - CCH VERTICAL DRIVE OVER CURRENT OR MOTOR DRIVER FAULTS 81 3812/81 3844. INSTANCES: 1 ->COULD BE CAUSED BY RAPID OPENING AND CLOSING OF MEL. CHECK WHICH MEL DEVICE IS CAUSING THE ISSUE. REFER TO KBA 00003318I. <br> MACHINE WAS POWEROFF A TIMES -> CHECK OTHER INSIGHTS FOR SOME DEL SITUATION TRIGGER THEM. |
| 2 2021/04/12 | - CCH VERTICAL DRIVE OVER CURRENT OR MOTOR DRIVER FAULTS 81 3812/81 3844. INSTANCES: 2 ->COULD BE CAUSED BY RAPID OPENING AND CLOSING OF MEL. CHECK WHICH MEL DEVICE IS CAUSING THE ISSUE. REFER TO KBA 00003318I. |
| 3 2021/04/09 | - CCH VERTICAL DRIVE OVER CURRENT OR MOTOR DRIVER FAULTS 81 3812/81 3844. INSTANCES: 1 ->COULD BE CAUSED BY RAPID OPENING AND CLOSING OF MEL. CHECK WHICH MEL DEVICE IS CAUSING THE ISSUE. REFER TO KBA 00003318I. <br> - MLC MOTOR-> A6 LEAF MOTOR (REPLACED OR LEAF STICKING (30 STB-A6I-109); PRIMARY AND SECONDARY ARE NOT MOVING AT ALL <br> - MLC MOTOR FAILURE PREDICTED ON LEAF A6->THIS LEAF MOTOR HAD SEVERAL ISSUES AND IS PREDICTED TO FAIL SOON. CHECK MOTOR; REPLACE MOTOR; CHECK RELATED COMPONENTS." <br> - MLC CONTROLLER HAS UNUSUAL AMOUNT OF INITIALIZATIONS (FROM ?->BAD?) ->  36 AS ->25 TO VOLT DASHBOARD FOR ADDITIONAL INFO->> |
| 4 2021/04/07 | - MLC MOTOR-> A6 LEAF MOTOR (REPLACED OR LEAF STICKING (30 STB-A6I-109); PRIMARY AND SECONDARY ARE NOT MOVING AT ALL <br> - MLC MOTOR FAILURE PREDICTED ON LEAF A6->THIS LEAF MOTOR HAD SEVERAL ISSUES AND IS PREDICTED TO FAIL SOON. CHECK MOTOR; REPLACE MOTOR; CHECK RELATED COMPONENTS." <br> - CCH VERTICAL DRIVE OVER CURRENT OR MOTOR DRIVER FAULTS 81 3812/81 3844. INSTANCES: 1 ->COULD BE CAUSED BY RAPID OPENING AND CLOSING OF MEL. CHECK WHICH MEL DEVICE IS CAUSING THE ISSUE. REFER TO KBA 00003318I. |
| 5 2021/04/06 | - CCH VERTICAL DRIVE OVER CURRENT OR MOTOR DRIVER FAULTS 81 3812/81 3844. INSTANCES: 2 10 INSTANCES->CALIBRATE THE BLADES AND INSPECT THE ASSEMBLY. REFER TO KBA 000032865 AND CAL-HT-PU2X (OR CAL-HT-1xPU); SECTION "CALIBRATE KV COLLIMATOR" <br> - KVS BLADE PRIMARY VS SECONDARY DEVIATION. KVBLADE X2 10 INSTANCES->CALIBRATE THE BLADES AND INSPECT THE ASSEMBLY. REFER TO KBA 000032865 AND CAL-HT-PU2X (OR CAL-HT-1xPU); SECTION "CALIBRATE KV COLLIMATOR" |

NEXT DAY NO ERROR ANYMORE

MLC INIT. AFTER MOTOR REPLACEMENT

ERROR ON LEAF MOTOR A6

FIG. 4K

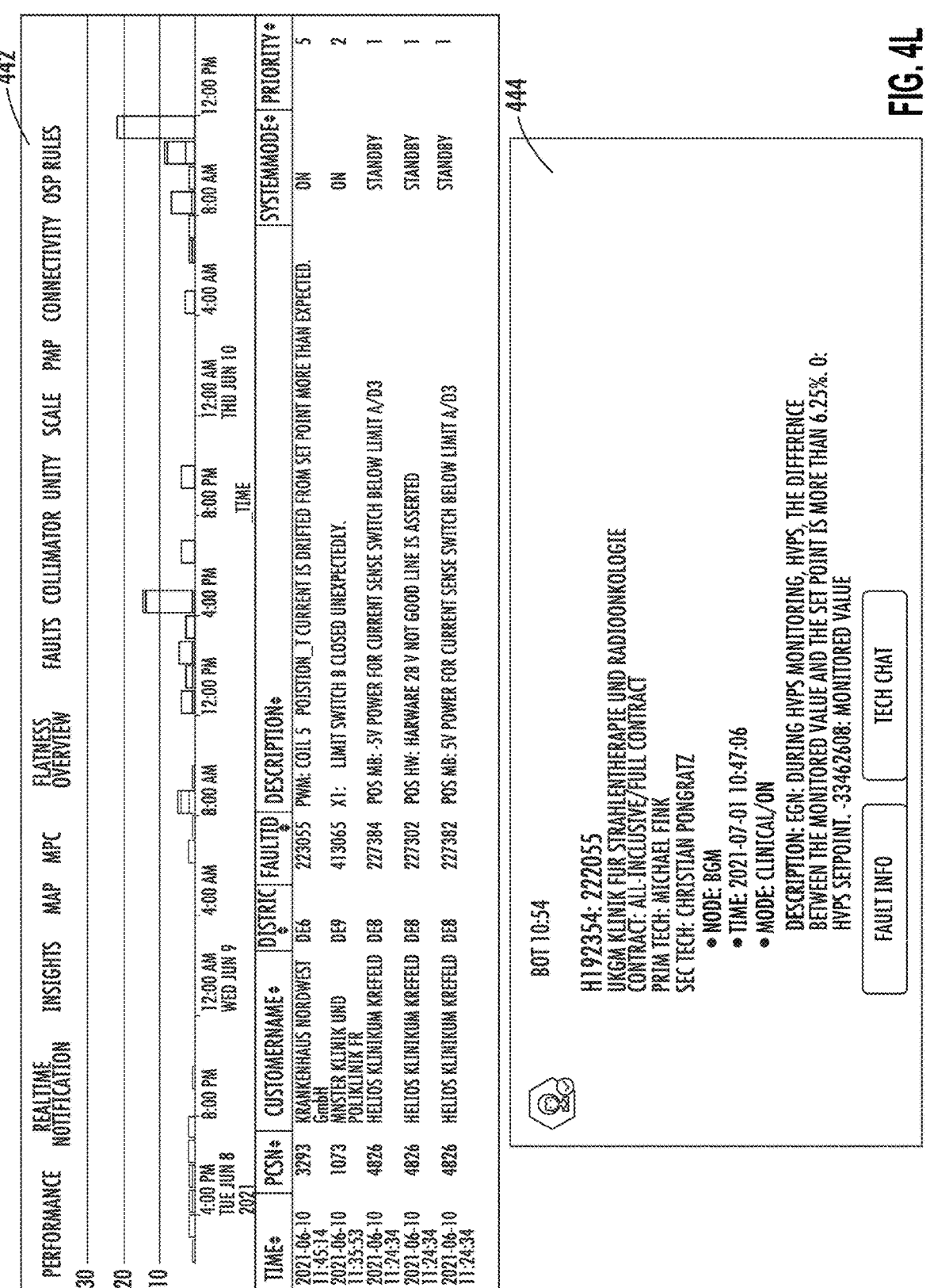

442

PERFORMANCE   REALTIME NOTIFICATION   INSIGHTS   MAP   MPC   FLATNESS OVERVIEW   FAULTS   COLLIMATOR   UNITY   SCALE   PMP   CONNECTIVITY   OSP RULES

| TIME◆ | PCSN◆ | CUSTOMERNAME◆ | DISTRIC◆ | FAULTID◆ | DESCRIPTION◆ | SYSTEMMODE◆ | PRIORITY◆ |
|---|---|---|---|---|---|---|---|
| 2021-06-10 11:45:14 | 3293 | KRANKENHAUS NORDWEST GmbH | DE6 | 223055 | PWM: COIL 5 POSITION_7 CURRENT IS DRIFTED FROM SET POINT MORE THAN EXPECTED. | ON | 5 |
| 2021-06-10 11:35:53 | 1073 | MASTER KLINIK UND POLIKLINIK FR | DE9 | 413065 | X1: LIMIT SWITCH B CLOSED UNEXPECTEDLY. | ON | 2 |
| 2021-06-10 11:24:34 | 4826 | HELIOS KLINIKUM KREFELD | DE8 | 227384 | POS MB: -5V POWER FOR CURRENT SENSE SWITCH BELOW LIMIT A/D3 | STANDBY | 1 |
| 2021-06-10 11:24:34 | 4826 | HELIOS KLINIKUM KREFELD | DE8 | 227302 | POS HW: HARDWARE 28 V NOT GOOD LINE IS ASSERTED | STANDBY | 1 |
| 2021-06-10 11:24:34 | 4826 | HELIOS KLINIKUM KREFELD | DE8 | 227382 | POS MB: 5V POWER FOR CURRENT SENSE SWITCH BELOW LIMIT A/D3 | STANDBY | 1 |

444

BOT 10:54

H192354: 222055
UKGM KLINIK FUR STRAHLENTHERAPIE UND RADIOONKOLOGIE
CONTRACT: ALL-INCLUSIVE/FULL CONTRACT
PRIM TECH: MICHAEL FINK
SEC TECH: CHRISTIAN PONGRATZ

● MODE: BGM
● TIME: 2021-07-01 10:47:06
● MODE: CLINICAL/ON

DESCRIPTION: EGN: DURING HVPS MONITORING, HVPS, THE DIFFERENCE BETWEEN THE MONITORED VALUE AND THE SET POINT IS MORE THAN 6.25%. 0: HVPS SETPOINT. -33462608: MONITORED VALUE

FAULT INFO      TECH CHAT

| STATIC VALUES | | | AXIS HOME SWITCH | | |
|---|---|---|---|---|---|
| VERSION⬥ | GUNFIL⬥ | KOSL⬥ | ROT⬥ | ENSW⬥ | ION ⬥ |
| 2.5.28.0 | 5,50 | 35.0 | 9,316 | 1,167 | 1,474 |

| CONFIG BY ENERGY | | |
|---|---|---|
| PARAMETERS⬥ | 6e⬥ | 6x⬥ |
| NOMINALTARGET | 0,0000 | 373,1437 |
| NOMINALFWP | 1,6700 | 1,6314 |
| AFC | 4,2980 | -2.703R |
| AFCCOEFF | 0,0000 | -0,0300 |
| RFDRIVERPOWER | 6,3710 | 5,8920 |
| AFCBALANCE | 0,0065 | 0,0833 |
| AFCSERVOPULSES | 35,0000 | 28,0000 |
| PFN | 6,0480 | 6,0480 |
| GUNWIDTH | 4,5000 | 4,4000 |
| GUNHV | -5 150,0000 | -15 000,0000 |

FIG. 4N

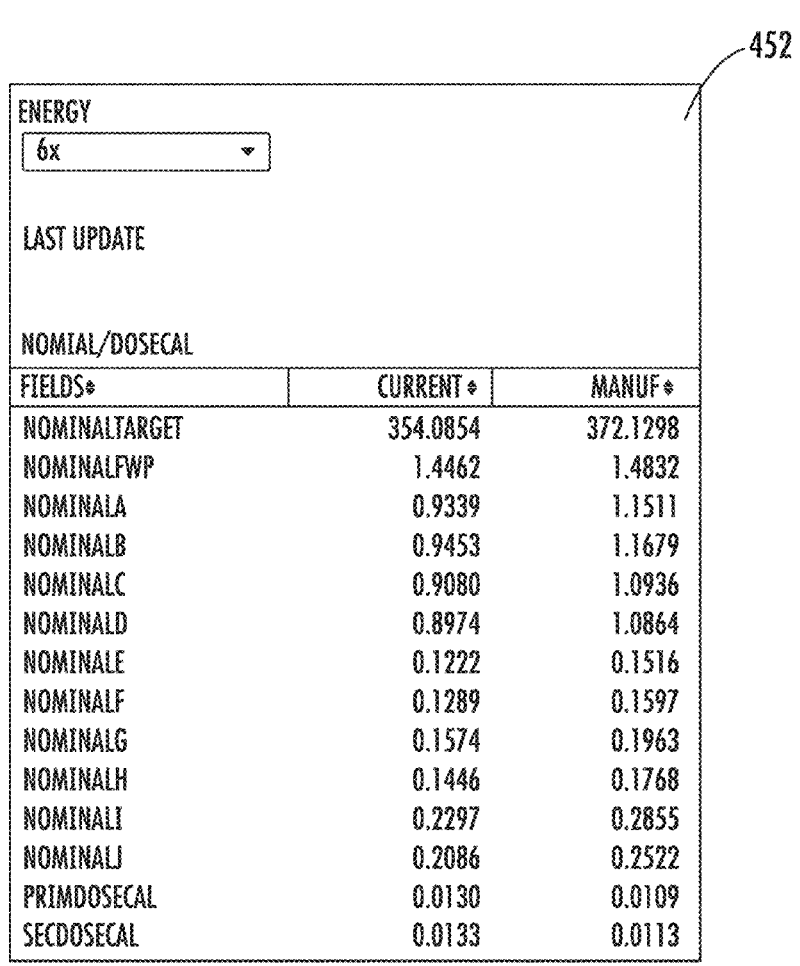
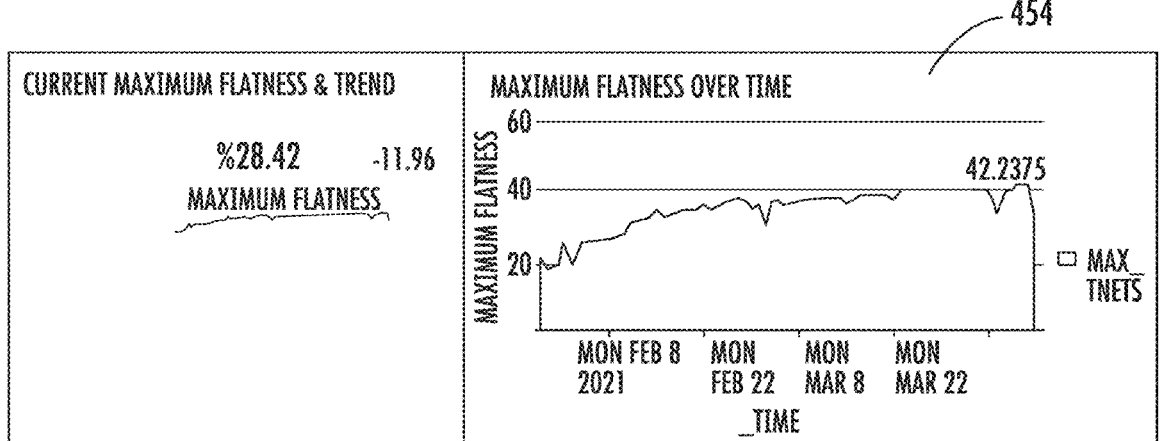
ENERGY
6x
LAST UPDATE
NOMIAL/DOSECAL
| FIELDS⬦ | CURRENT⬦ | MANUF⬦ |
|---|---|---|
| NOMINALTARGET | 354.0854 | 372.1298 |
| NOMINALFWP | 1.4462 | 1.4832 |
| NOMINALA | 0.9339 | 1.1511 |
| NOMINALB | 0.9453 | 1.1679 |
| NOMINALC | 0.9080 | 1.0936 |
| NOMINALD | 0.8974 | 1.0864 |
| NOMINALE | 0.1222 | 0.1516 |
| NOMINALF | 0.1289 | 0.1597 |
| NOMINALG | 0.1574 | 0.1963 |
| NOMINALH | 0.1446 | 0.1768 |
| NOMINALI | 0.2297 | 0.2855 |
| NOMINALJ | 0.2086 | 0.2522 |
| PRIMDOSECAL | 0.0130 | 0.0109 |
| SECDOSECAL | 0.0133 | 0.0113 |
452
454
CURRENT MAXIMUM FLATNESS & TREND
%28.42    -11.96
MAXIMUM FLATNESS
MAXIMUM FLATNESS OVER TIME
42.2375
MAX_TNETS
MON FEB 8
2021    MON
FEB 22    MON
MAR 8    MON
MAR 22
_TIME
FIG. 40

460

| BGM | VERSION | SERIAL |
|---|---|---|
| NAME ⬍ | VERSION ⬍ | SERIAL ⬍ |
| BGM-POS-MEZZ-PCB | 100049108-03 | 421205392 |
| BGM-POS-PCB | 100015403-10 | 381201268 |
| BGM-RFSPS-PCB | 100014281-05 | 71300967 |
| BGM-CONT-MEZZ-PCB | 100048874-03 | 061301821 |
| BGM-PCB | 100048880-04 | 061301655 |
| BGM-PWM-PCB | 100014271-07 | 51300670 |
| BGM-EGN-PCB | 100014276-09 | 51300647 |
| BGM-MOD-PCB | 100014286-06 | 41303495 |
| BGM-CONT-PCB | 100014266-13 | 021760620 |
| BGM-EGN-GUNDRIVER-PCB | 100025258-00 | 0 |

462

GLOBAL BGM CONFIGURATION                    EXPORT ▾   ...
STATISTICS FOR BGM CONFIGURATIONS WORLDWIDE

ENERGY                          PARAMETER
[ 6x        ▾ ] [×]       [ GUNWIDTH   ▾ ] [×]      [SUBMIT]  HIDE FILTERS

| AVERAGE | STDev | UPPER LIMIT | LOWER LIMIT |
|---|---|---|---|
| 4.591 | 0.254 | 5.099 | 4.083 |

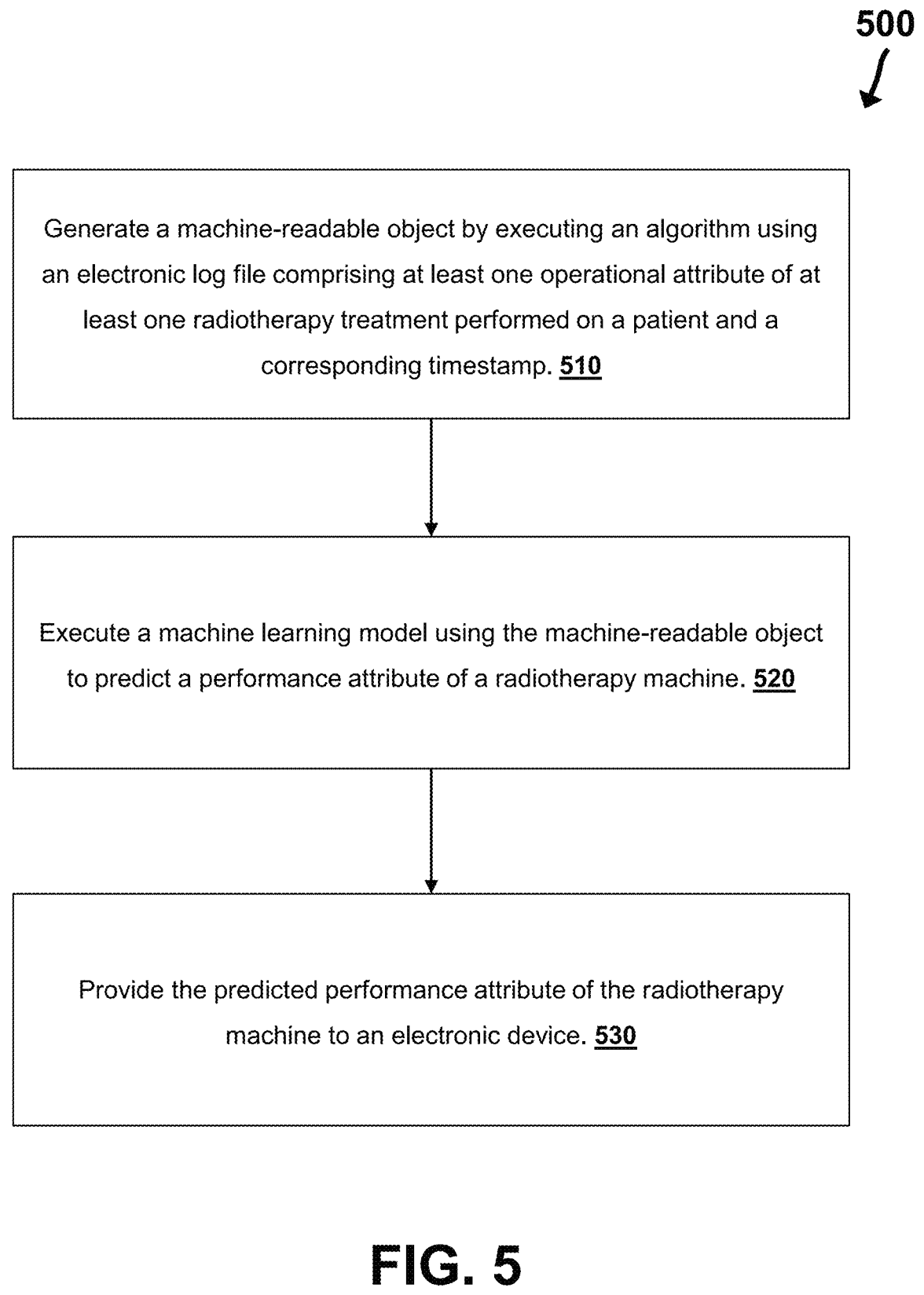

Generate a machine-readable object by executing an algorithm using an electronic log file comprising at least one operational attribute of at least one radiotherapy treatment performed on a patient and a corresponding timestamp. 510

Execute a machine learning model using the machine-readable object to predict a performance attribute of a radiotherapy machine. 520

Provide the predicted performance attribute of the radiotherapy machine to an electronic device. 530

FIG. 5

MACHINE LEARNING FOR INTELLIGENT RADIOTHERAPY DATA ANALYTICS

TECHNICAL FIELD

This application relates generally to using data analysis techniques to diagnose and recommend remediation procedures for radiotherapy machines.

BACKGROUND

Radiotherapy (radiation-based therapy) is used as a cancer treatment to emit high doses of radiation that can kill cells or shrink a tumor. Radiotherapy machines are implemented using a diverse range of complex mechanical components and software, and often require routine maintenance to operate correctly. Conventional maintenance procedures often require in-depth troubleshooting by highly specialized maintenance workers in order to both diagnose and rectify an issue with radiotherapy machines. Downtime experienced radiotherapy machines incurs a cost to the hospital operating the radiotherapy machines, and can interrupt patient treatment plans that would otherwise be carried out.

Rapid rectification of issues or failures in radiotherapy machines is therefore important to both operators of radiotherapy machines and patients that require radiotherapy treatment. However, radiotherapy machines may generate highly specialized log files indicating faults, errors, or other maintenance related messages. It is important to detect issues with radiotherapy machines and other machines related to therapy machines to improve treatment outcomes for patients. Further, the volume of information generated by radiotherapy machines is impracticable to analyze manually, and provides limited insight into potential future issues that could arise during regular operation.

SUMMARY

For the aforementioned reasons, there is a desire for a system that can rapidly and accurately analyze information and log files produced through the operation and maintenance of radiotherapy machines. To overcome the deficiencies described above, it is desirable to train and execute a machine learning model that can rapidly and accurately analyze and categorize information produced by radiotherapy machines. Instead of utilizing manual review processes, which are tedious and often inconsistent, the systems and methods described herein may execute machine learning models to identify both current and potential future issues of radiotherapy systems, and can quickly identify to a maintenance person exactly how to address these issues.

The system may execute specialized algorithms to convert unstructured log files and information sources into machine-readable objects that can be readily processed by machine-learning models. The machine-readable objects may be re-structured into databases (e.g., NoSQL databases) and served to maintenance workers according to their characteristics. Structuring previously unstructured machine data can allow for custom user interfaces, such as chat bots or other maintenance interfaces, to quickly provide an indicate both current and potential future issues with radiotherapy machines. In addition, the system may execute a machine learning model, which may be trained using supervised learning techniques, on the machine data to predict future performance or future operational characteristics of radiotherapy machines. The predictions generated by the machine learning models can be provided both to maintenance workers and operators of radiotherapy machines to aide in preventative maintenance, and thereby improve overall machine uptime.

Furthermore, the systems and methods of this technical solution may utilize natural language processing techniques to allow maintenance workers or operators of the radiotherapy machines to access information in chat-based software. The chat-based software can receive queries or questions related to identified radiotherapy machines in a natural language, and respond with an electronic message that includes appropriate and up-to-date analytical information related to the query. Doing so can enable users to access information generated by the systems and methods described herein without requiring in-depth knowledge of machine-generated log files, machine learning processes, database storage platforms, or other platforms.

In one embodiment, a method comprises generating, by a processor, a machine-readable object by executing an algorithm using an electronic log file comprising at least one operational attribute of a radiotherapy machine and a corresponding timestamp; executing, by the processor, a machine learning model using the machine-readable object to predict a performance attribute of the radiotherapy machine; and providing, by the processor to an electronic device, the predicted performance attribute of the radiotherapy machine.

Providing the predicted performance attribute may include instructing, by the processor, the electronic device to display an input element configured to receive a query in natural language; and instructing, by the processor, the electronic device to display a graphical element representing the predicted performance attribute.

The predicted performance attribute may indicate performance of at least one part of the radiotherapy machine that satisfies a threshold.

The operational attribute may include at least one of an orientation of at least one component of the radiotherapy machine, attribute of a radiation emitted by the radiation therapy machine, voltage consumed by the radiotherapy machine, a number of cycles operated by one or more components of the radiotherapy machine, or a number of workflow interruptions corresponding to the radiotherapy machine.

The predicted performance attribute may correspond to a remaining estimated time or a remaining number of treatments before a failure associated with the radiotherapy machine.

The machine learning model may be trained based on historical machine-readable objects and corresponding performance attributes.

The method may include identifying, by the processor, one or more unperformed tasks associated with the radiotherapy machine based on the machine-readable object; and providing, by the processors to the electronic device, the one or more unperformed tasks associated with the radiotherapy machine based on the machine-readable object.

The method may include determining, by the processor, that the radiotherapy machine is due for preventative maintenance based on the predicted performance metric.

The method may include receiving, by the processor from the electronic device, an identifier of the radiotherapy machine via a natural language query; and retrieving, by the processor, the machine-readable object by accessing an electronic database using the identifier of the radiotherapy machine.

The machine learning model may be trained using a supervised learning technique.

In another embodiment, a system comprises a processor configured to execute instructions stored on a non-transitory computer-readable medium to generate a machine-readable object by executing an algorithm using an electronic log file comprising at least one operational attribute of a radiotherapy machine and a corresponding timestamp; execute a machine learning model using the machine-readable object to predict a performance attribute of the radiotherapy machine; and provide the predicted performance attribute of the radiotherapy machine.

The instructions when executed by the processor may cause the processor to provide the predicted performance attribute by instructing the electronic device to display an input element configured to receive a query in natural language; and instructing the electronic device to display a graphical element representing the predicted performance attribute.

The instructions when executed by the processor may cause the processor to identify one or more unperformed tasks associated with the radiotherapy machine based on the machine-readable object; and provide the one or more unperformed tasks associated with the radiotherapy machine based on the machine-readable object to the electronic device.

The instructions when executed by the processor may cause the processor to determine that the radiotherapy machine is due for preventative maintenance based on the predicted performance metric.

The instructions when executed by the processor may cause the processor to receive, from the electronic device, an identifier of the radiotherapy machine via a natural language query; and retrieve the machine-readable object by accessing an electronic database using the identifier of the radiotherapy machine.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIGS. 2A-2C illustrate example information that is generated by radiotherapy machines and processed using the techniques described herein, according to an embodiment;

FIG. 5 illustrates an example flow diagram of another executed in a system for processing information generated by radiotherapy machines, according to an embodiment.

DETAILED DESCRIPTION

Figure 1:
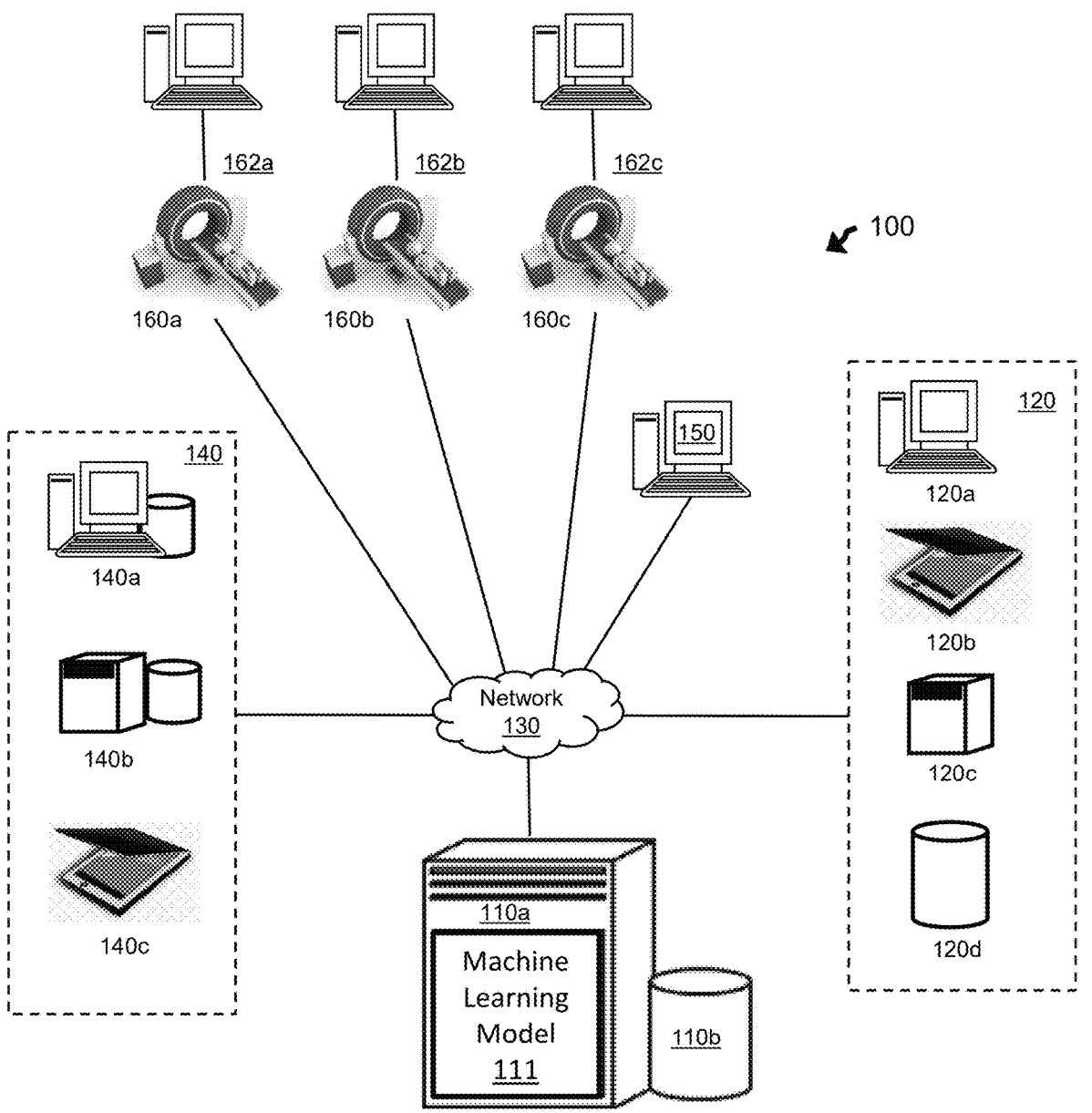
FIG. 1 illustrates components of a machine learning system that processes data generated by radiotherapy machines, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Radiotherapy machines are powerful and complex machines that are crucial for the treatment of certain cancers. During operation, radiotherapy machines may generate large logs and information files that include diagnostic information, machine status information, and other data relating to the operational status of the radiotherapy machine. While some of this information may be useful in maintenance procedures, much of the generated information may be unrelated to issues currently experienced by the radiotherapy machine. This excess information, coupled with varying data formats across different devices and environments, may make it challenging to parse and identify information that is useful for particular use cases, such as preventative maintenance or failure diagnostics.

While management of radiotherapy machines may be performed remotely (e.g., by implementing networked analysis of produced data), doing so presents further challenges. The volume of information produced by radiotherapy machines en masse is impracticable to analyze in conventional analysis systems. For example, the volume of relevant information generated by radiotherapy machines can exceed 300 Gb of data daily. This information is highly valuable to understand the conditions, problems, and overall utilization of operating radiotherapy machines. Traditionally, analyzing this information would require manual review through standard text-reading applications, which are unsuitable for viewing and providing insights to large amounts of information.

The systems and methods described herein overcome these limitations by using algorithms to translate the information generated by radiotherapy machines into machine-readable objects on an on-going basis, which can be recorded to databases for further analysis. The machine-readable objects can indicate information about required actions that should be taken on particular radiotherapy machines, or can be used in further analytical processes, such as machine learning, to derive additional insights.

The system can receive information directly from operators of radiotherapy machines, for example, from computing devices in communication with or operating as part of the radiotherapy machines. The received information can include any type of log file, diagnostic data, or data produced during the operation of a radiotherapy machine. The systems and methods can execute one or more algorithms on the received data to generate structured information that is suitable for storage in one or more electronic database, such as a NoSQL database. Machine learning models may then be executed on the machine-readable objects to derive additional insights into the operation and predictive performance of the radiotherapy machines.

In addition, the processed data can be presented to users, such as maintenance worker or operators of radiotherapy machines, in graphical user interfaces on electronic devices. The analyzed data may be presented as part of a chat bot that receives natural language queries and generates human-understandable responses that include actionable information related to the query. Insights can be provided that indicate performance trends of radiotherapy devices over extended periods of time, in addition to day-to-day operational information. The use of the processing techniques described herein, in connection with natural language processing techniques for presentation of processed data, provide improved access and visualization of data that would otherwise be impracticable to analyze.

As will be described below, a server (referred to herein as the analytics server) can execute algorithms to generate machine-readable objects (e.g., data structures or files) that may be provided to further analytical processes, such as machine learning models In a non-limiting example, the analytics server may execute a machine learning model over the machine-readable objects to generate a prediction metric for a radiotherapy machine, which may indicate a need for preventative maintenance or provide a solution or diagnosis for a machine failure event. FIG. 1 is an example of components of a system in which the analytics server operates. Various other system architectures that may include more or fewer features may utilize the methods described herein to achieve the results and outputs described herein. Therefore, the system depicted in FIG. 1 is a non-limiting example.

FIG. 1 illustrates components of a system 100 for intelligent radiotherapy data analytics, according to an embodiment. The system 100 may include an analytics server 110a, system database 110b, a machine learning models 111, electronic data sources 120a-d (collectively electronic data sources 120), end-user devices 140a-c (collectively end-user devices 140), an administrator computing device 150, and medical devices 160a-c (collectively medical device(s) 160) each associated with a respective one of the medical device computers 162a-c (collectively medical device computer(s) 162). Various components depicted in FIG. 1 may belong to a radiotherapy clinic at which patients may receive radiotherapy treatment, in some cases via one or more radiotherapy machines located within the clinic (e.g., medical device 160). The above-mentioned components may be connected to each other through a network 130. Examples of the network 130 may include, but are not limited to, private or public local-area-networks (LAN), wireless LAN (WLAN) networks, metropolitan area networks (MAN), wide-area networks (WAN), and the Internet. The network 130 may include wired and/or wireless communications according to one or more standards and/or via one or more transport mediums.

The system 100 is not confined to the components described herein and may include additional or other components, not shown for brevity, which are to be considered within the scope of the embodiments described herein.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models 111 (including artificial intelligence and/or machine learning models) for automated processing of radiotherapy operational information. The analytics server 110a may execute various algorithms to translate raw operational information generated by the medical devices 160 into machine-readable objects that can be stored and processed by other analytical processes as described herein. The electronic platform may include graphical user interfaces (GUI) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computers, and the like. The electronic platform may display various analytical information in user interfaces, such as the user interfaces shown in FIGS. 4A-4R. The information displayed by the electronic platform can include, for example, operational information generated by the medial devices 160.

Figure 4A:
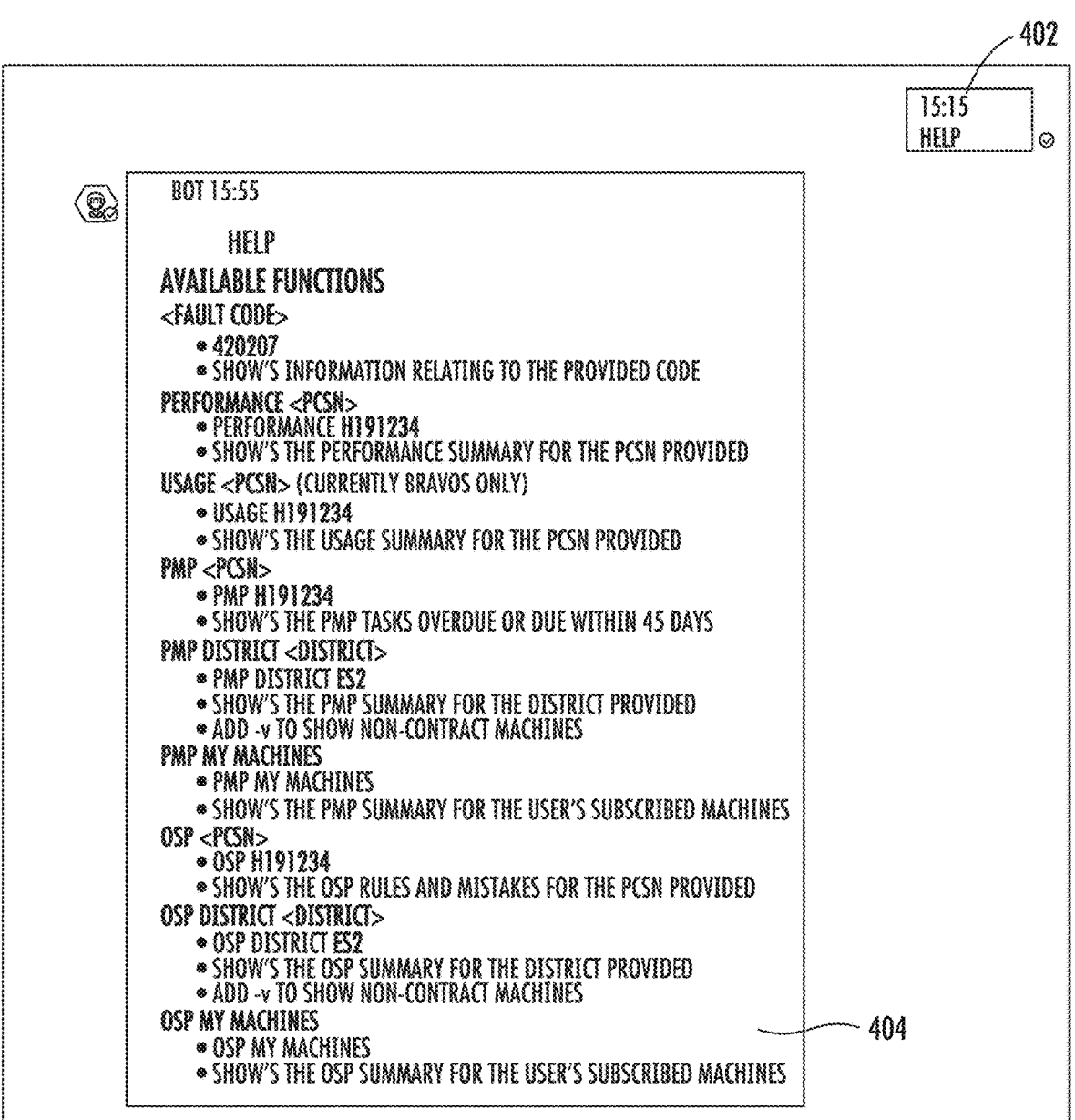
FIGS. 4A-R illustrate example user interfaces that present information relating to radiotherapy machines following the processing steps described herein, according to an embodiment.
Figure 4B:
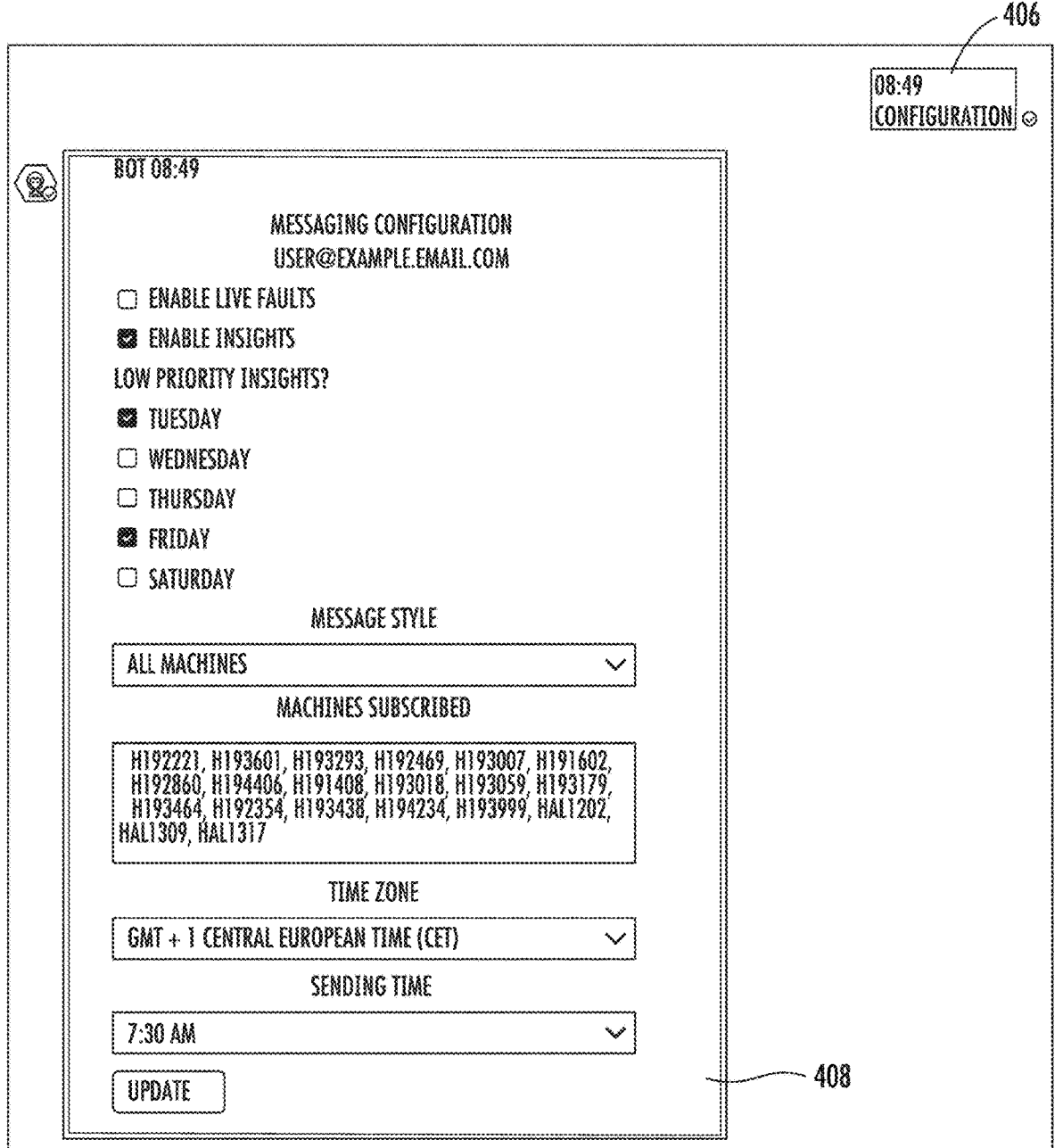

The analytics server 110a may also execute various software components that accept queries or requests from the other computing devices of the system 100, such as the electronic data sources 120, the end-user devices 140, and/or the administrator computing device 150. In a non-limiting example, a maintenance operator for medical devices 160 may access the platform, and provide interactions or requests to access operational information related to the medical devices 160 to which the maintenance operator is assigned. The analytics server 110a may execute a natural language processing software that can receive queries in a natural language (e.g., conversational queries from the maintenance operator) and provide generate appropriate responses. Some examples of the electronic platform displaying responses generated by natural language processing software are shown in FIGS. 4A and 4B. The maintenance operator may access any information provided by the analytics server 110a that is generated from the raw operational information provided by the medical devices 160.

The analytics server 110a may host a website accessible to users operating any of the electronic devices described herein (e.g., end users, medical professionals, maintenance operators), where the content presented via the various webpages may be controlled based upon each particular user's role or viewing permissions. The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120, end-user devices 140, the administrator computing device 150, and/or the medical device computer 162. Different users may use the website to view and/or interact with displayed content.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly authenticating the user) match an appropriate set of credentials that identify and authenticate the user.

The analytics server 110*a* may generate and host webpages based upon a particular user's role within the system 100. In such implementations, the user's role may be defined by data fields and input fields in user records stored in the system database 110*b*. The analytics server 110*a* may authenticate the user and may identify the user's role by executing an access directory protocol (e.g., LDAP). The analytics server 110*a* may generate webpage content that is customized according to the user's role defined by the user record in the system database 110*b*. For example, a particular user may have authorization to access to information generated by the analytics server 110*a* for a specified set of medical devices 160.

The analytics server 110*a* may receive operational information, such as electronic log files, from a medical device 160 or the medical device computer 162, or retrieve such data from a data repository, analyze the data in accordance with the techniques described herein, and display the results on the electronic platform. For instance, in a non-limiting example, the analytics server 110*a* may query and retrieve operational information or electronic log files from the database 120*d* and combine the operational information with additional information received from the medical device 160 or the medical device computer 162. Additionally, the analytics server 110*a* may execute one or more algorithms, such as rule-based algorithms or machine learning models, to process the operational information into machine-readable objects for storage in a database, such as the database 110*b*.

The analytics server 110*a* may execute various machine learning models 111 (e.g., machine learning models trained to generate predicted performance metrics for the medical devices 160, machine learning models trained using supervised learning techniques, etc.) to analyze the machine-readable objects generated from the raw electronic log files. The analytics server 110*a* may then display the results via the electronic platform on the administrator computing device 150 and/or the end-user devices 140.

The electronic data sources 120 may represent various electronic data sources that contain, retrieve, and/or access data associated with a medical device 160, such as operational information, electronic log files, or electronic configuration files. For instance, the analytics server 110*a* may use the clinic computer 120*a*, medical professional device 120*b*, server 120*c* (associated with a physician and/or clinic), and database 120*d* (associated with the physician and/or the clinic) to retrieve/receive data associated with the medical device 160.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic server 140*b*, and a medical processional device 140*c*. Even though referred to herein as "end user" devices, these devices may not always be operated by end users. For instance, the clinic server 140*b* may not be directly used by an end user. However, the results stored onto the clinic server 140*b* may be used to populate various GUIs accessed by an end user via the medical professional device 140*c*.

The administrator computing device 150 may represent a computing device operated by a system administrator. The administrator computing device 150 may be configured to display radiation therapy treatment attributes generated by the analytics server 110*a* (e.g., various analytic metrics determined during training of one or more machine learning models and/or systems); monitor various models 111 utilized by the analytics server 110*a*, electronic data sources 120, and/or end-user devices 140; review feedback; and/or facilitate training or retraining (calibration) of the machine learning models 111 that are maintained by the analytics server 110*a*.

The medical device 160 may be a radiotherapy machine configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally). The medical device 160 may also be in communication with a medical device computer 162 that is configured to display various GUIs discussed herein. For instance, the analytics server 110*a* may display the results predicted by the machine learning models 111 onto the computing devices described herein.

During operation of the medical device 160, the medical device 160 may generate operational information, such as electronic machine log files, electronic configuration log files, and/or electronic event log files. In a non-limiting example, this operational information can include the electronic log files shown in FIGS. 2A-2C. The operational data can include, for example, information relating to the operations of software processing modules executing at the radiotherapy machine, information related to faults experienced by the radiotherapy machines, information relating to procedures performed using the radiotherapy machine, information relating to images captured by the radiotherapy machine, information relating to service interruptions experienced by the radiotherapy machines, information relating to a radiation source of the radiotherapy machine, or information relating to voltages of the radiotherapy machine, among others.

Figure 2A:
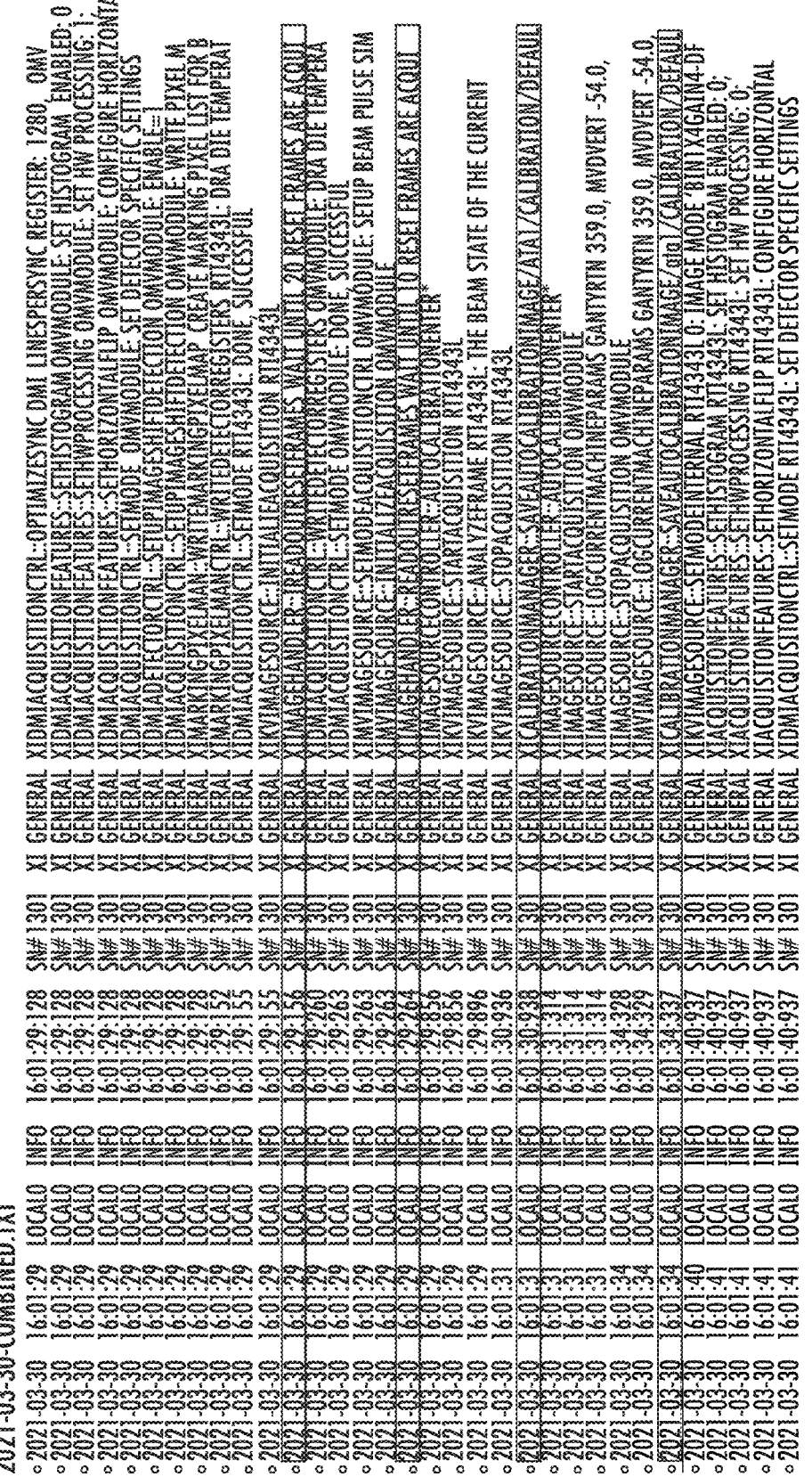

Referring to FIG. 2A, depicted is an example screenshot 200*a* of a portion of an example log file generated by a medical device, such as the medical device 160 described in connection with FIG. 1. As shown, the information in the log file can be stored in chronological order, and can indicate various conditions and operations performed by software executing on the radiotherapy machine. Information in the log file may be stored with information that causes a text editor or an application displaying the log file to present an information in a different color, or with a highlight annotation. While these annotations may be helpful in discerning some information in the log file, information that may be relevant to potential faults or other actionable events are impracticable to analyze using conventional techniques.

A similar log file is shown in FIG. 2B, which shows an example screenshot 200*b* of a portion of a configuration log file of a medical device, such as the medical devices 160 described in connection with FIG. 1. The example configuration log file is stored as a derivative of a markup language, such as an extensible markup language (XML). While the information in configuration log files may be displayed in a standard text-based formula, the information stored in the configuration file is stored at a level of complexity that is similarly impracticable to analyze. The information in the configuration file may be specific to the medical device.

Figure 2C:
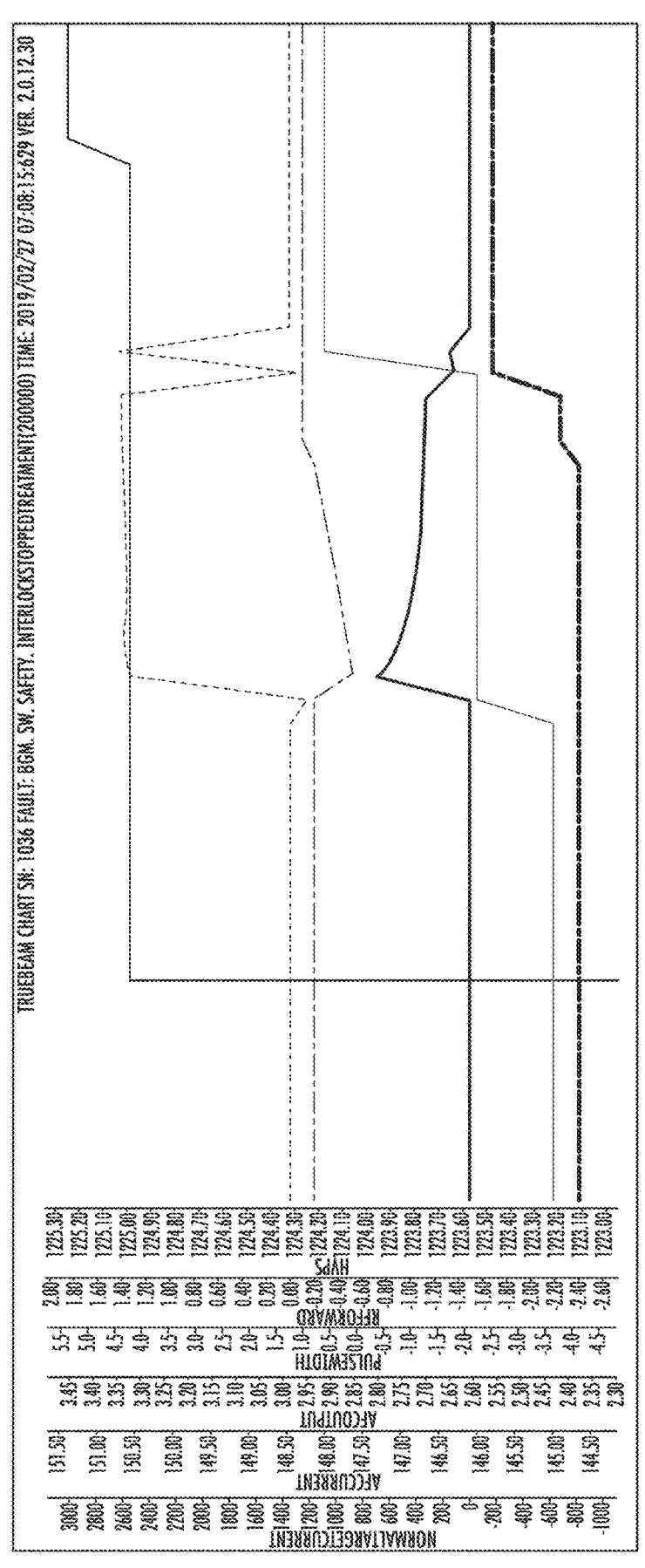

FIG. 2C shows a screenshot 200*c* of an event log file generated during operation of the medial device, such as the medical device 160 described in connection with FIG. 1. The event log can display a time-series line graph of signals generated from various channels whose values change during the operation of the medical device. While some of the information presented in the event log file may be readable to an expert familiar with a specific medical device, it would be similarly impracticable to analyze time-series data for long periods of medical device operation.

Referring back to FIG. 1, in operation, the medical devices 160 may operate according to their intended functionality, and generate raw operational information continuously, at periodic intervals, and/or in response to particular events (e.g., in response to a medical professional activating the medical device 160). The raw operational information may take the form of one or more log files, which can be transmitted to, or retrieved by, the analytics server 110*a* for storage. The medical device 160 or the medical device computer 162 may transmit the operational information to another computer device, such as a hospital computing device or the data repository 120*d*. Any new raw operational information stored at the hospital computing device or the data repository 120*d* may be transmitted to, or retrieved by, the analytics server 110*a* on a periodic basis, for example once per day in a data synchronization process.

The analytics server 110*a* may execute one or more algorithms to translate the raw operational data gathered from one or medical devices 160 into corresponding machine-readable objects. The analytics server 110*a* may store the machine-readable objects in association with respective information corresponding to a time of an event indicated in a machine-readable object (e.g., a failure event, a service interruption event, etc.), or an identifier of the respective medical device 160 from which the machine-readable object was generated. The machine-readable objects may be presented directly to a user of the analytics server 110*a* (e.g., via the electronic platform as described herein), or may be used in further analytical processes using the machine learning models 111.

Machine learning models 111 may be stored in the system database 110*b* and may correspond to individual medical devices 160, individual types of machine-readable objects, different types of analytical output data, or otherwise different sets of radiotherapy machines (e.g., radiotherapy machines that are located at individual radiotherapy clinics, are located in different geographical regions, that generate different types of raw operational data, etc.).

In various embodiments, machine learning models 111 use one or more deep learning engines to generate predicted performance attributes of the medical devices 160. Although exemplified neural networks trained using supervised learning techniques, it should be understood that any alternative and/or additional machine learning model(s) may be used to implement similar learning engines. The deep learning engines can include processing pathways that are trained during a training phase. Once trained, deep learning engines may be executed (e.g., by the analytics server 110*a*) to generate predicted performance attributes for medical devices 160.

As described herein, the analytics server 110*a* may store machine learning models 111 (e.g., neural networks, random forest, support vector machines, regression models, recurrent models, etc.) in memory. The analytics server 110*a* may retrieve the models and train the machine learning models to predict performance metrics of the medical devices 160 described herein. Various machine learning techniques may involve "training" the machine learning models to predict (e.g., estimate the likelihood of) each performance attributes of a medical device 160, including supervised learning techniques, unsupervised learning techniques, or semi-supervised learning techniques, among others. In a non-limiting example, the predicted performance attributes may indicate that the performance of one or more parts (e.g., mechanical or hardware components) of the medical device 160 that satisfies a threshold, such as a use threshold. For example, the threshold can indicate that a particular component is overused or needs to be replaced. The machine learning models 111 can therefore be used to generate indications of components of medical devices 160 that have failed, are failing, or will fail within a predetermined time period. In another non-limiting example, the predicted performance metric may indicate a remaining estimated time or a remaining number of treatments before a failure associated with the radiotherapy machine. Each medical device 160 (or the components thereof) may be rated for a predetermined number of cycles or operations. The machine learning models 111 may therefore be trained to generate an indication of how many cycles remain before a medical device 160 requires service, based on the machine readable objects generated by the analytics server 110*a*.

One type of deep learning engine is a deep neural network (DNN). A DNN is a branch of neural networks and consists of a stack of layers each performing a specific operation, e.g., convolution, pooling, loss calculation, etc. Each intermediate layer receives the output of the previous layer as its input. The beginning layer is an input layer, which is directly connected to or receives an input data structure that includes the data items in one or more machine-readable objects, and may have a number of neurons equal to the data items in one or more machine-readable objects provided as input. For example, a machine readable object may be a data structure, such as a list or vector, which includes a number of data fields include data extracted from the raw data generated by the medical devices 160. Each neuron in an input layer can accept the contents of one data field as input. The analytics server 110*a* may pre-process the machine-readable objects (e.g., through an encoding process) such that the data fields may be accepted as input to the machine learning models 111 described herein.

A next set of layers are can include any type of layer that may be present in a DNN, such as a convolutional layer, a fully connected layer, a pooling layer, or an activation layer, among others. Some layers, such as convolutional neural network layers, may include one or more filters. The filters, commonly known as kernels, are of arbitrary sizes defined by designers. Each neuron can respond only to a specific area of the previous layer, called receptive field. The output of each convolution layer can be considered as an activation map, which highlights the effect of applying a specific filter on the input. Convolutional layers may be followed by activation layers to apply non-linearity to the outputs of each layer. The next layer can be a pooling layer that helps to reduce the dimensionality of the convolution's output. In various implementations, high-level abstractions are extracted by fully connected layers. The weights of neural connections and the kernels may be continuously optimized in the training phase.

In practice, training data may be user-generated through observations and experience to facilitate supervised learning. For example, training data may be extracted from past radiotherapy treatments provided to prior patients, historic quality assurance procedures performed on radiotherapy machines, previous mock treatments executed at radiotherapy machines, information produced while testing radiotherapy machines, or other information produced by radiotherapy machines. Training data may be pre-processed via any suitable data augmentation approach (e.g., normalization, encoding, any combination thereof, etc.) to produce a new dataset with modified properties to improve model generalization using ground truth.

Training the machine learning models 111 may be performed, for example, by analyzing historic maintenance log files and corresponding machine-readable objects of previously serviced medical devices 160. For example, when a maintenance worker services a medical device, an electronic service record may be generated that indicates a particular fault that was serviced in the machine. This service record can serve as a "ground truth" for machine failure, which may be associated with raw operational information generated from the serviced medical device 160 prior to the service event or a detected failure event. This raw information may be converted into machine-readable objects using the processes described herein, and associated with the ground-truth failure information for the medical device 160, which can operate as a label. The labeled machine-readable objects generated from historic electronic log files can be used as training data for the machine learning models 111, for example, in a supervised learning process. However, it should be understood that other training techniques may also be used in training the machine learning models 111.

Inputs to the models 111 include a set of machine-readable objects generated from raw data produced by a medical device 160. The machine-readable objects can be predetermined objects that include information of a particular type, and can be generated by the analytics server 110a using the processes described herein. Model outputs may include a confidence score indicating a likelihood that the medical device 160 corresponds to a particular performance attribute (e.g., in need of preventative maintenance, is within a threshold of cycles before maintenance is required, is exhibiting or will likely exhibiting a predetermined fault, etc.).

Figure 3:
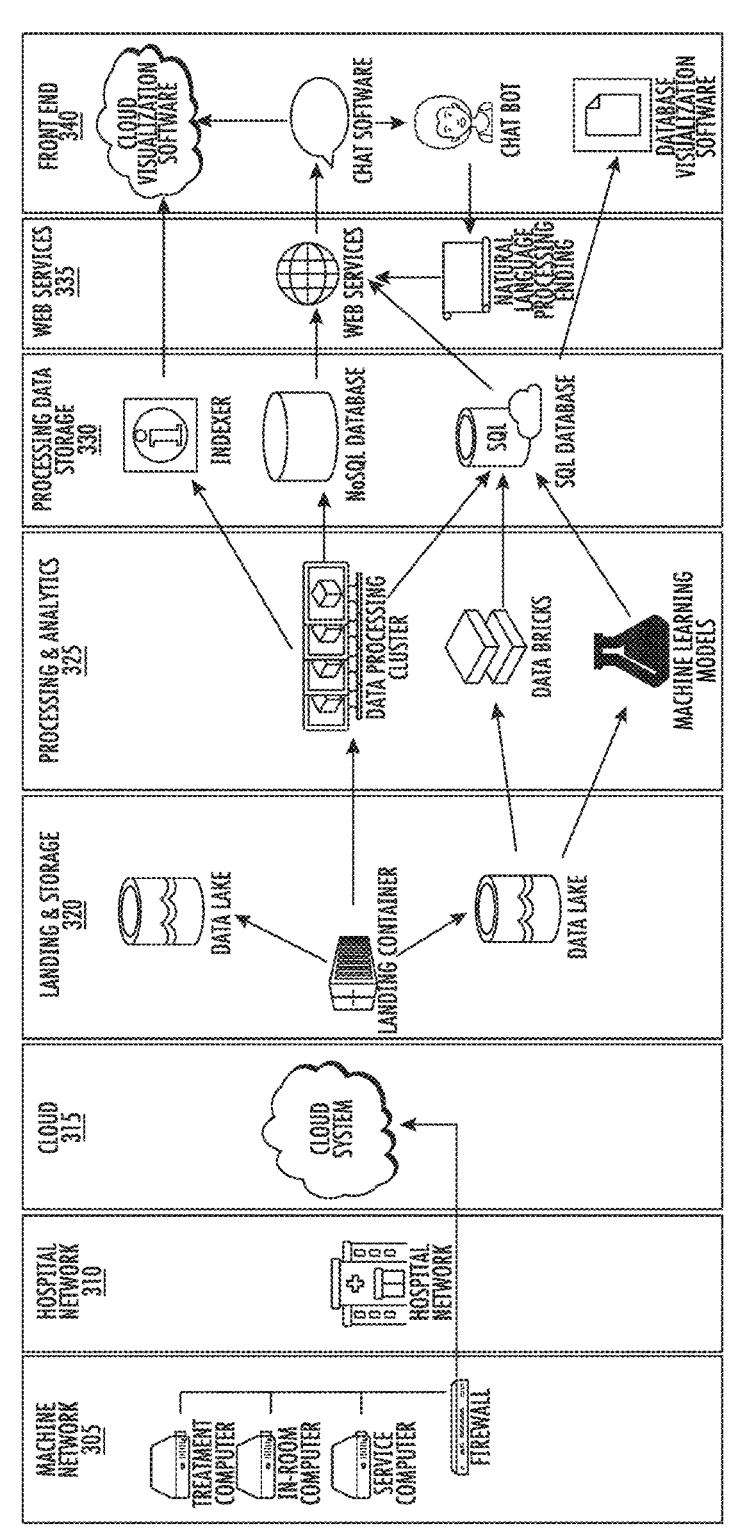
FIG. 3 illustrates a process flow diagram of a process executed in a system for processing information generated by radiotherapy machines, according to an embodiment.

Referring to FIG. 3, depicted is an example data flow diagram 300 that shows how raw operational data generated by medical devices, such as the medical devices 160 described in connection with FIG. 1, may be processed, stored, and presented to users. As shown starting at the machine network 305, various computers operating on a hospital network 310 (e.g., which can be similar to and include any of the functionality of the network 130 described in connection with FIG. 1) can generate raw operational data, such as the raw operational data shown in FIGS. 2A, 2B, and 2C. These procedures may be performed by any number of hospitals or treatment locations. The several computers that generate the raw operational data at a hospital network may communicate with the hospital network at stage 310 via a firewall, or a similar network security layer.

The hospital network may communicate the raw operational data to a cloud system at stage 315. The cloud system may be an external cloud system that specializes in accepting and storing large amounts of raw information. The hospital network may communicate the raw data using one or more application programming interfaces (APIs) provided by or associated with the cloud computing system. At stage 315, the cloud computing system may receive raw data generated at many hospitals or treatment centers over a number of different geographic areas. In other words, the cloud computing system may receive aggregate information from medical devices that operate in many different locations and that are associated with largely different maintenance or operational staff.

The cloud system, upon receiving the data from the hospitals, may store or transfer the raw data to a "landing container," at stage 320, which may be a computing system that is responsible for maintaining or updating one or more data lakes. A data lake is a system or repository of data that is stored in a raw format, for example as binary large objects (blobs), files, or other types of data structures. The landing container computing system can update the data lake by storing the raw data generated by the medical devices in retrievable formats, for example, and may store the information in association with a timestamp indicating when the raw data was generated. The data lakes may then be accessed by the various computing systems described herein to convert the raw data into machine-readable objects.

For example, at stage 325, various computing devices or data processing clusters may execute algorithms over the raw data in the data lakes described herein to generate the machine-readable objects. For example, the computing systems at stage 325 may parse through newly added raw data to extract information of interest, and generate corresponding machine-readable objects by parsing through the raw data using various rule-based algorithms. Some non-limiting examples of machine-readable objects can include patients, plans, fields, and execution times, which relate to particular patients treated by a particular medical device. Such machine-readable objects may be referred to as "Clinical Utilization Objects." Machine-readable objects may also include statistics (e.g., frequency of various events, patient treatment information, or operational characteristics of the medical devices), data models (e.g., including any machine learning models 111 described in connection with FIG. 1), and time-series data, such as the time-series data shown in the event log of FIG. 2C. In addition, the machine-readable objects can include machine data split by groups of medical devices, and records of maintenance events or maintenance related information (e.g., detected faults, detected failures, detected service interruptions, etc.). Other types of machine-readable objects may include some raw data, which may be used for future processing, or informational data that is used for cataloguing. The data processing clusters at stage 325 may process information produced by the medical devices in a distributed configuration, such that the raw data is split into a cluster and processed in parallel using, for example, a producer-consumer pattern. The data processing clusters (e.g., which can be or can include the analytics server 110a) may execute one or more machine learning models, such as the machine learning models 111 described in connection with FIG. 1, over the raw data to generate predicted performance attributes as described herein. Various insights (e.g., the predicted performance attributes) generated by the machine learning models may also be stored as machine-readable objects at stage 325.

Once the machine-readable objects have been processed and analyzed in at stage 325, the generated machine-readable objects (which may include insights such as the predicted performance metrics for one or more medical devices) may be stored in one or more repositories at stage 330, for later visualization and machine-learning processes. Some examples of data repositories can include a SPLUNK CLOUD PLATFORM, which provides a Software-as-a-Service platform for searching, analyzing, and visualizing structured information. Other examples of data repositories can include SQL Servers, which may allow for fast indexing and retrieval for further machine-learning and POWER BI processes as described herein. In addition, the data repositories can include a non-relational database such as an AZURE COSMOS DB or a NoSQL database. The non-relational databases may be used to store or maintain document information and configuration files for automated chat bots, as described herein. The computing systems operating at stage 330 can utilize one or more APIs associated with the respective data repositories to communicate and store the generated machine-readable objects. The computing systems operating at stage 330 may also perform blob storage for long term storage or archiving of the machine-readable objects.

The machine-readable objects stored in the data repositories at stage 330 may be accessed by users via computing devices executing stages 335 and 340. At stage 335, various web services may provide web-based user interfaces to access one or more of the machine-learning objects corresponding to one or more medical devices. Stage 335 may also include executing a natural language processing engine, such LANGUAGE UNDERSTANDING (LUIS). Users may execute various software programs to access the web services or the natural language processing engines provided at stage 335, to query and view actionable information relating to the medical devices. The software executing at stage 340 can include, for example, communication software (e.g., MICROSOFT TEAMS) or other chat-based software, natural language processing bots (e.g., which may execute as part of the communication software, etc.), web browsers, database access software, and edge-level machine-learning processes.

The software at stage 340 may be executed at any of the computing devices described herein, including phones, tablets, or personal computers. The software can enable users to subscribe to particular medical devices, such that users are authorized to view and receive information relating to the medical devices to which they are subscribed. For example, the software may provide notifications or alarms to a user subscribed to a medical device when a critical condition is detected at that medical device. Communication software may include one or more chat or information channels that are each associated with a respective machine. The web services or the natural language processing services provided at stage 335 can push information to the channels (e.g., conditions, predicted performance attributes, etc.) that is associated with the respective medical device.

The machine learning processes that are executed at the edge can be one or more of the machine learning models 111 described in connection with FIG. 1. The machine learning models may be trained at a back-end server or another high-performance computing device, and subsequently provided to and executed on end-user devices (e.g., the end-user devices 140) for real-time analytical information. Some examples of outputs provided by the machine learning models executed at the edge can include indications of potential gas leaks, indications of a target failure due to a hole, temperature predictions, indications of potential fan failures, or indications of power-supply failures, among others. The software executing at the stage 340 can include POWER BI. The software and user interfaces provided to the user at stage 340 can be a part of the electronic platform provided by the analytics server described in connection with FIG. 1.

Some examples of user interfaces provided by the electronic platform of the analytics server 110a are shown in FIGS. 4A-4R. Any of the medical devices referenced with respect to any of FIGS. 4A-4R can include the medical devices 160 described in connection with FIG. 1. Referring to FIG. 4A, depicted is an example chat interface provided by communication software that executes an automated chat bot. As shown, the user has provided a message 402, which reads "Help". In response, the automated chat bot (shown as "Bot") provides a response message 404 that includes a list of available functions available to the user. The first item in the list is a "<fault code>," which allows a user to communicate a specific fault code (e.g., produced by a medical device, such as the medical devices 160 described in connection with FIG. 1) to the automated chat bot and receive a response that includes specific information relating to that fault code. The automated chat bot can access information in a data repository including information that is indexed by fault code (e.g., a fault code identifier), and retrieve the information for display.

Other commands provided by the automated chat bot can include, for example, the "Performance" command, which provides a performance summary for a particular medical device 160. Each medical device, which may be the medical devices 160 described in connection with FIG. 1, can be associated with a respective identifier (an identifier of a medical device may be referred to as a "PCSN" of a medical device). The identifier can be provided by a user as an argument for the performance command, which causes the automated chat bot to retrieve one or more machine-readable objects that include corresponding performance information for the identified medical device. The performance can be, for example, a percentage of treatment cycles that were interrupted by one or more faults. Similar processes can be performed for the "Usage" command, which returns usage information related to the identified medical device (e.g., a remaining number of cycles for the medical device or the components thereof), and the PMP (planned maintenance program) command, which returns information about upcoming, pending, or overdue maintenance tasks due for the identified medical device. The OSP-related commands ("OSP <PCSN>", "OSP District <District>", and "OSP My Machines") return information relating to OSP rules or an OSP summary for specific medical devices. For example, medical devices may be identified by geographic region (e.g., a district), or organized as a subscription model, where the user is authorized or subscribed to one or more specified medical devices. It will be appreciated that the commands shown in FIG. 4A are not an exhaustive list of commands, and that a number of other commands are possible.

Referring to FIG. 4B, depicted is a depicted is an example chat interface provided by communication software that executes an automated chat bot. As shown, the user has provided a message 406, which reads "Configuration." In response, the automated chat bot provides a response message 408 that includes a list of available configuration options available to the user. The configuration options are presented in a graphical user interface with one or more user-selectable user interface elements, such as fields, check boxes, and drop-down fields. The Enable Live Faults field enables the user to receive messages from relating to detected faults from the automated chat box. The Enable Insights field enables the user to receive insights (e.g., predicted performance attributes), for example, as notifications or messages from the automated chat bot. The notifications can be transmitted as one or more messages in the chat application. The list of days under the "Low Priority Insights?" heading indicates days on which notifications relating to low priority insights will be received from the automated chat bot. The Message Style drop down box allows responses from the automated chat bot to reference all machines (e.g., all subscribed machines) when providing notifications or retrieving responses to queries, or to only provide information relating to medical devices with available insights.

The Machines Subscribed field enables a user to provide a list of device identifiers that each correspond to a respective medical device. This can allow a user to only receive notifications or insights that are related to a specified set of medical devices. The Time Zone field allows a user to configure a time zone that is closest to them, and set a corresponding Sending Time that configures a time of day at which the automated chat bot can being sending messages related to the subscribed medical devices. The "New User" button allows the user to create a user profile, for example, in a data repository such as the data repository 110*b* described in connection with FIG. 1, such that the user profile includes the specified configuration data. The "Update" button causes the automated chat bot to update the corresponding user profile in the data repository with the updated configuration settings.

Figure 4C:
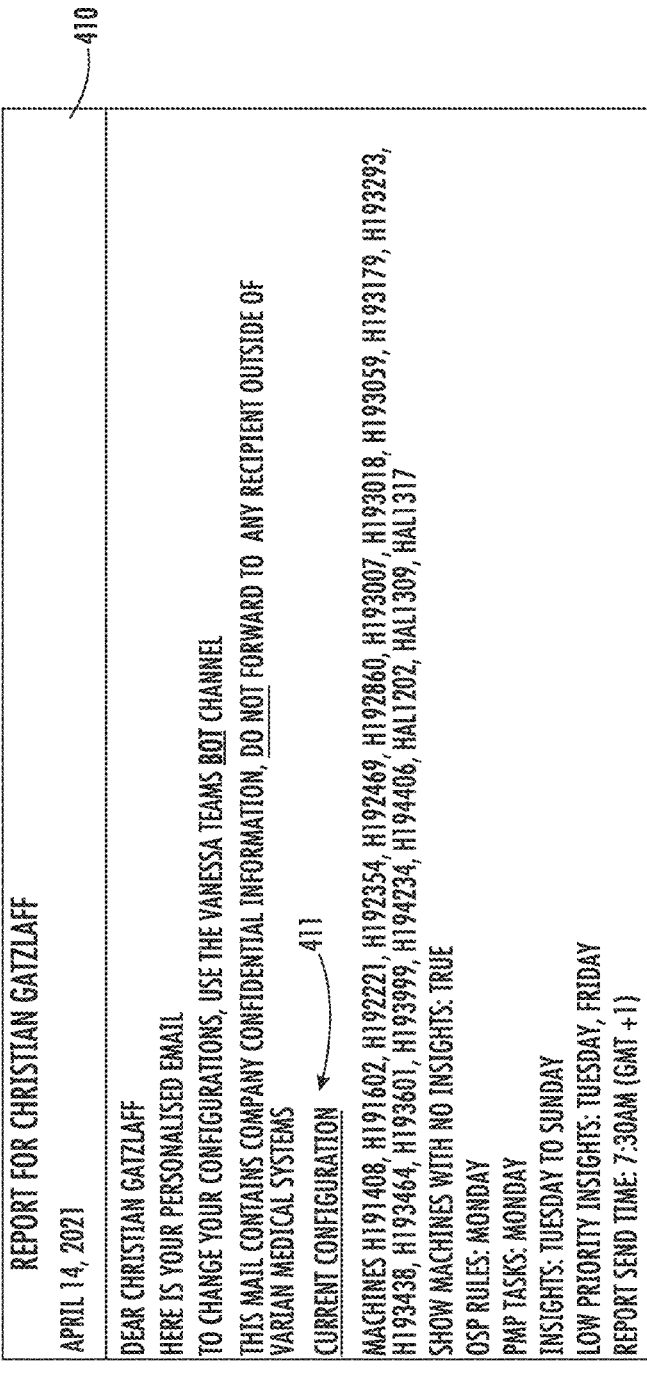

Referring to FIG. 4C, is an example daily report email 410 transmitted to a user of an analytics server, such as the analytics server 110*a* described in connection with FIG. 1. As shown, the report email 410 provides details related to the user profile (e.g., a list of subscribed machines, whether notifications from machines with no insights will be provided, a day that OSP rules will be implemented, a day that PMP tasks will be implemented, days on which insights of normal or high priority will be shown, days on which low-priority insights will be shown, or a time of day at which reports will be sent). The report email 410 can include a "Current Configuration" link 411, which when actuated causes an electronic device displaying the report email 410 to navigate to the web page 412 shown in FIG. 4D, which shows a personal analytics interface for the user. As shown in FIG. 4D, the web page 412 includes a list of active machines and corresponding customer information and performance information for each machine. The web page 412 can list data for each of the machines to which the user is subscribed. The performance data can be determined from the one or more machine-readable objects generated by the analytics server in response to detecting object failures.

Referring to FIG. 4E, depicted is a portion 414 of the report email, which is generated based on the performance and insight machine-readable objects associated with each medical device to which the user is subscribed. The portion 414 of the report email shows a list of medical devices to which the user is subscribed. The list can include a set of header lines 415 for each medical device, which can include a medical device identifier and a Customer description. The header line is a link within the report email, which when interacted with navigates the user to a monitoring dashboard 416 for the corresponding medical device. The report email can also periodically (e.g., once per week) include an overview 418 about the previous weeks performance for each medical device to which the user is subscribed. The previous performance information can provide information about PMP tasks, OSP Rules (e.g., archiving information for local raw data), and connectivity to the data-gathering processes described herein (e.g., whether raw operational data is transmitted from the medical device).

Referring to FIG. 4F, depicted are example user interfaces 420 and 422 that can be provided by the automated chat bot described herein. The automated chat bot may receive queries, for example, relating to different aspects of one or more medical devices. As described herein above, one such command is the "OSP" command, which provides status information relating to archive rules for raw data, e.g., which are maintained or archived for by the medical devices. The OSP command can take an identifier of a medical device, which may include wildcard characters, as an argument. In response, the automated chat bot can generate a response by accessing one or more machine-readable objects that include OSP data related to the identified medical device. An example response message to the OSP command is shown in the user interface 420. The "Performance" command can include similar arguments, and cause the automated chat bot to retrieve information related the performance of an identified medical device. An example response message to the Performance command is shown in the user interface 422.

Figure 4G:
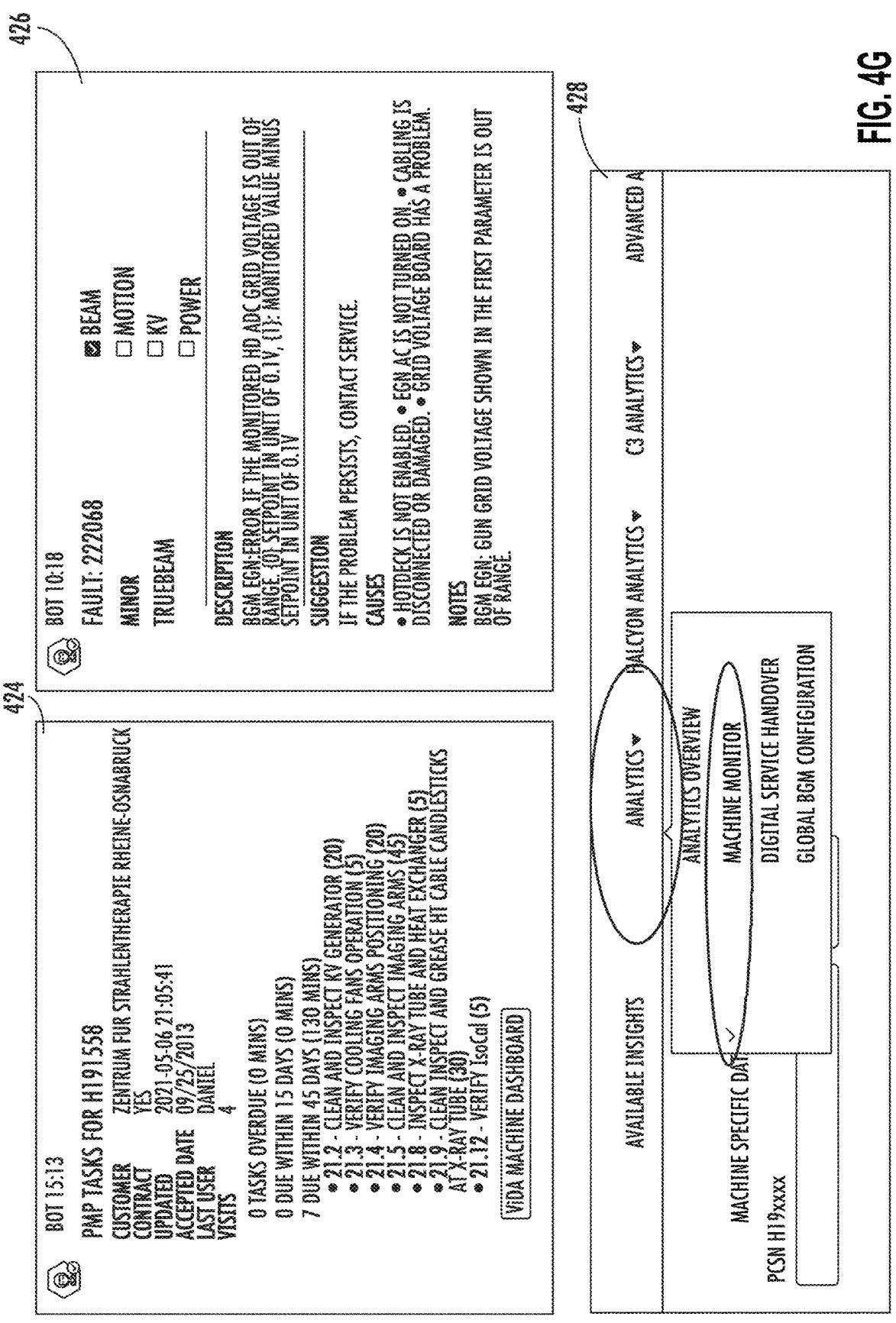

Referring to FIG. 4G, depicted are example user interfaces provided by the systems and methods herein. The user interfaces 424 and 426 may be provided in response to commands input to the automated chat bot described herein. As described herein above, one such command is the "PMP" command, which provides information relating to a planned maintenance program for an identified medical device. The PMP command can take an identifier of a medical device, which may include wildcard characters, as an argument. In response, the automated chat bot can generate a response by accessing one or more machine-readable objects that include PMP data related to the identified medical device. An example response message to the PMP command is shown in the user interface 424. Another command that may be provided to the automated chat bot is the "<Fault ID>" command, which allows a user to provide a fault ID as input to the automated chat bot, which retrieves one or more data records for that fault code and provides a user interface showing a description, a suggestion, causes, and notes for the identified fault ID. An example response message to the "<Fault ID> command is shown in the user interface 426, which shows the response for the fault ID "222068".

The user interface 428 shows a web-based user interface that allows a user of the analytics server to access PMP pre-site preparation information from one or more medical devices. As shown in the interface 428, the user can select the machine monitor, and enter in a corresponding identifier of the medical device the user intends to monitor. Upon entering an identifier, the web-based interface can display information relating to the overall health of the medical device and any identified areas of concern (e.g., insights derived from the machine-readable objects, etc.). Examples of interfaces shown in response to providing the identifier of the medical device are shown in FIGS. 4H and 4I.

Figure 4I:
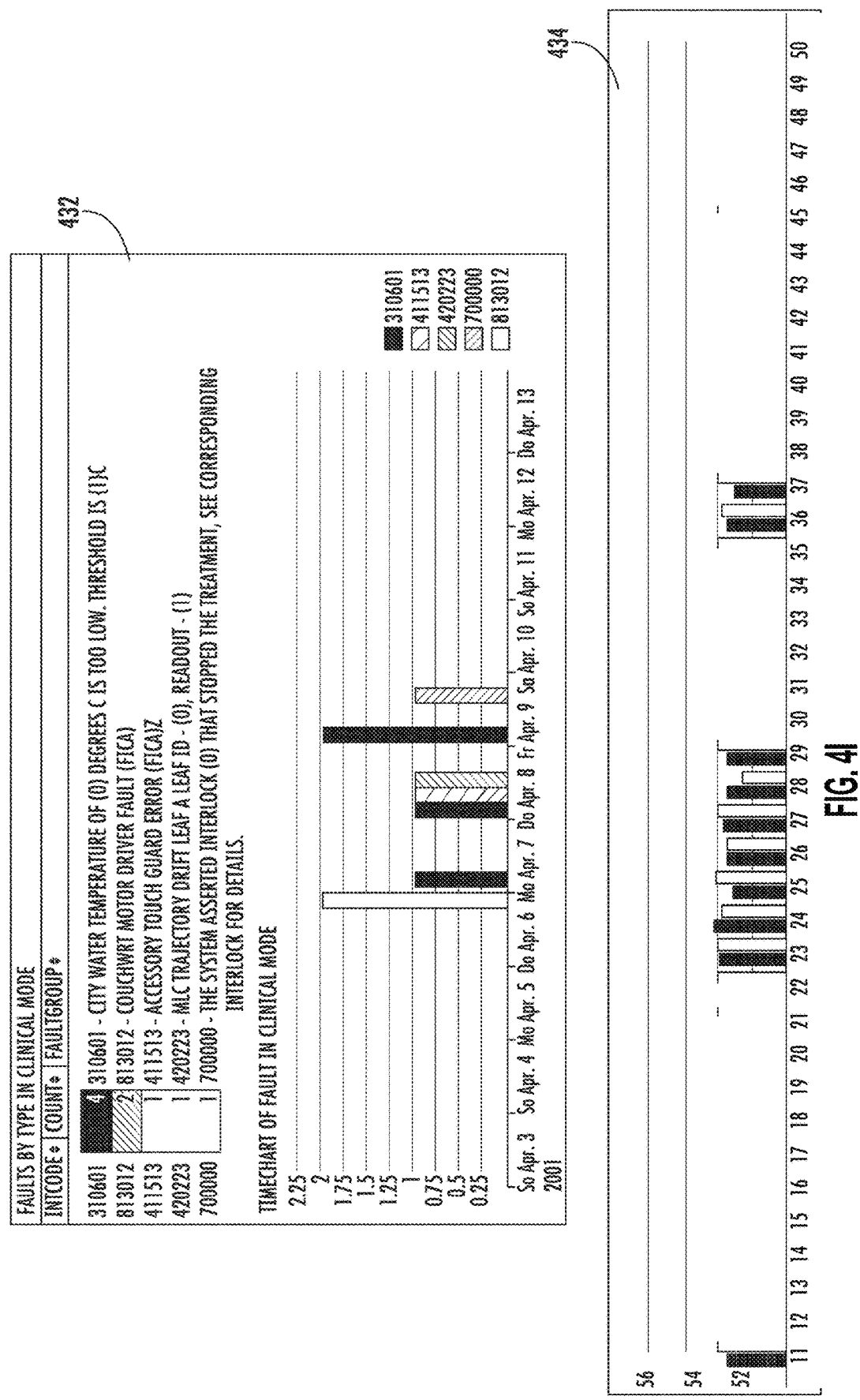

Referring to FIGS. 4H and 4I, depicted are user interfaces 430, 432, and 434, which each include information relating to insights identified from the machine-readable objects that are presented in response to accessing the machine monitor web-based interface. The user interface 430 shown in FIG. 4H includes a list of insights related to the identified medical device, and corresponding suggested actions. Insights identified by the analytics server may be associated with a priority value (e.g., HIGH or LOW priority). As shown in FIG. 4I, the user interface 432 shows example fault statistics for an identified medical device. The user interface 432 can show a fault code, a count of each type of detected fault, and a group to which each fault corresponds. In addition, a time-based chart for the identified faults may be generated and displayed as part of the user interface 432. The user interface 434 shows information relating to the collimator of the medical device (e.g., when the medical device is a radio therapy machine). The user interface can include a time-series graph of multi-leaf collimator (MLC) values that may indicate the necessity for T-Nut replacements. The example MLC backlash values shown in the user interface 434 may be larger than the values from a PMP backlash test. Additional user interfaces shown in response to accessing the Machine Monitor web-based interface are depicted in FIGS. 4J and 4K.

Figure 4J:
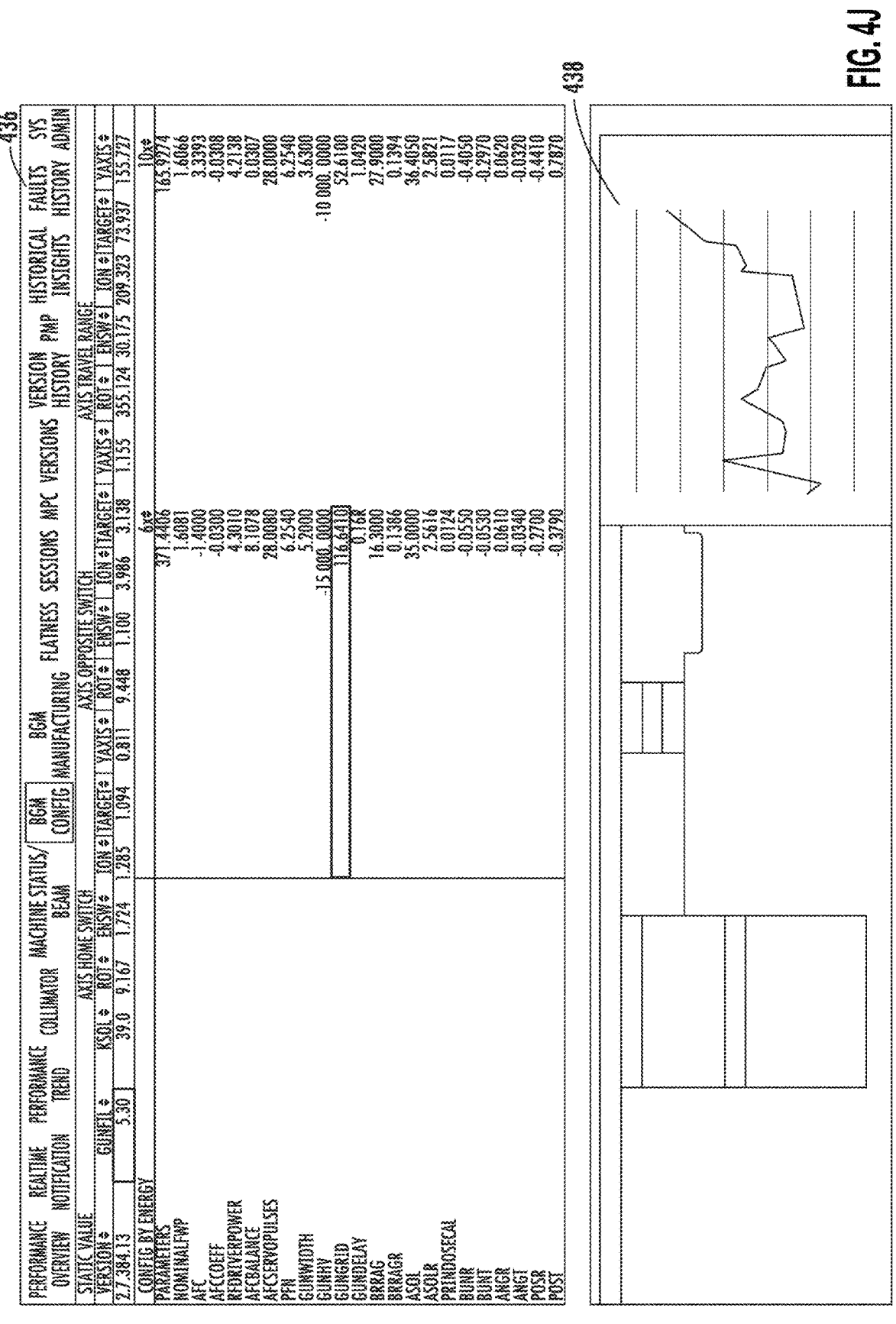

Referring to FIGS. 4J and 4K, depicted are user interfaces 436, 438, 440, and 441, which each include information relating to insights identified from the machine-readable objects that are presented in response to accessing the Machine Monitor web-based interface. The user interface 436 includes information related to a beam generation and monitoring (BGM) configuration for an identified medical device. The user interface 436 can include a list of BGM configuration values, which under normal circumstances should be highlighted in green, indicating they are within their normal operating parameters. If a BGM configuration value is highlighted in red, then this indicates that value is outside the normal operating parameters and therefore it should be investigated. The user interface 438 includes information relating to machine performance check (MPC) tests performed on the identified medical device. The list of recent MPC tests can indicate whether each test passed (e.g., highlighted in green), failed (e.g., highlighted in red) or was above a predetermined warning level (e.g., a marginal pass highlighted in yellow). Interacting with the each affected group provides information relating to the affected sub-group, which may indicate a trend of the selected sub-group over a period of time. The user interface 440 includes a list of PMP tasks that are overdue for an identified medical device. The user interface 441 includes a list of historical insights generated from the machine-readable objects associated with the identified medical device. The list of historical insights can indicate a severity and a frequency (e.g., a number of reoccurrences) for each insight, including whether an insight indicates a fault that interrupted patient treatment.

Referring to FIG. 4L, depicted is a user interface 442, which includes a list of real-time notifications provided by radiotherapy devices. The notifications can be updated periodically (e.g., every 2 minutes, etc.), and can updates can be received from a notification system executed by the analytics server. For example, the analytics server can monitor incoming data from the medical devices to determine whether a fault condition or a notification condition has occurred. If a notification has occurred, the analytics server can update the user interface 442 with information relating to the notification (e.g., a fault, an error, a treatment interruption, etc.). Also depicted in FIG. 4L is the user interface 444, which is a fault notification provided by the automated chat bot described herein. As described herein, if the user has configured the Live Faults option for the automated chat bot, the analytics server can provide notifications of faults that occurred in medical devices to which the user is subscribed via the automated chat bot. The example user interface 444 shows the fault notification for a medical device with the identifier H192354. As shown, the user interface 444 shows the medical device identifier, the fault ID, the customer name, the contract type, names of a Primary and a Secondary Field Service Engineer, and detailed information about the detected fault. The name of the customer is can be a link to the Machine Monitor page of the medical device reporting the issue. The "Fault Info" button at the bottom of the message, when actuated, can cause the automated chat bot to provide a message with more detailed information about the fault. The "Tech Chat" button will open a new communication chat session in the communication software with the Primary or Secondary Field Service Engineer associated with the medical device.

Figure 4M:
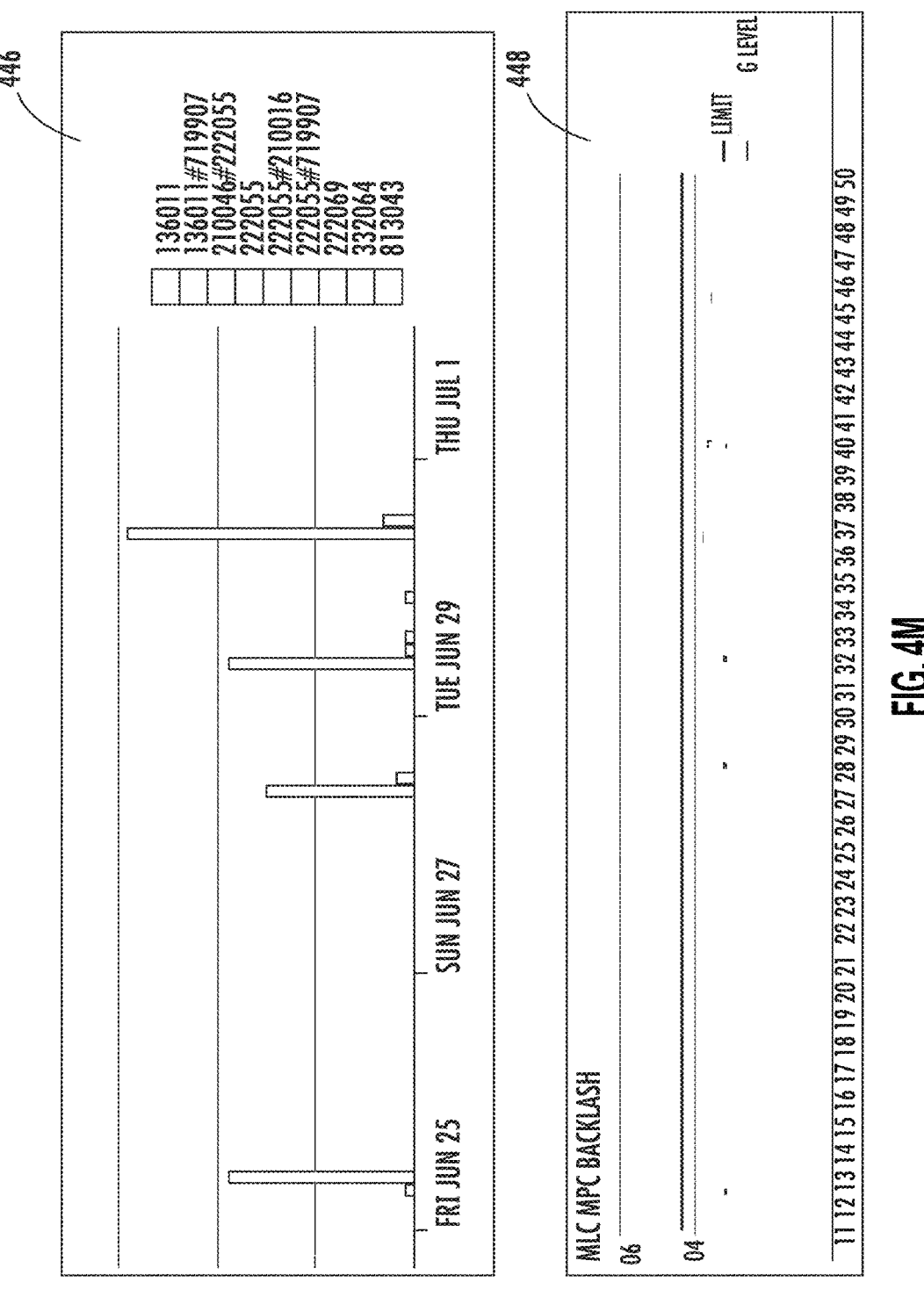

Referring to FIGS. 4M and 4N, depicted are additional user interfaces 446, 448, and 450 provided as part of the Machine Monitor web interface. The user interface 446 shows a time-series fault history for various detected faults that occurred in an identified medical device. The user interface 446 can be similar to the user interface 432 described in connection with FIG. 4I. The user interface 448 shows an interface that display MLC MPC data for an identified medical device. The user interface 448 can be similar to the user interface 434 described in connection with FIG. 4G. The user interface 448 can include data such as leaf backlash, Trajectory and Pri/Sec faults, and more detailed information about specific MLC faults. As depicted in FIG. 4N, the user interface 450 shows a BGM configuration for an identified medical device. The user interface 450 can be similar to the user interface 436 described in connection with FIG. 4J.

Referring to FIG. 4O, depicted is an example user interface 452 showing BGM manufacturer information. The BGM manufacturer information can include the original BGM configuration values when the medical device was manufactured, which may be different than the BGM configuration values shown in the user interface 450 of FIG. 4N. FIG. 4O also depicts a user interface 454, which includes flatness information for the identified medical device. The user interface 454 can display displays Current Maximum Flatness trends and Maximum Flatness trends over time. When 212022 and/or 212023 "flatness" faults at a medical device accompany an upward flatness trend over time indicated in that medical device, then a proactive Ion Chamber replacement is recommended. The analytics server can detect such corresponding occurrences and provide a suggestion to the user to replace the Ion Chamber of the medical device.

Figure 4P:
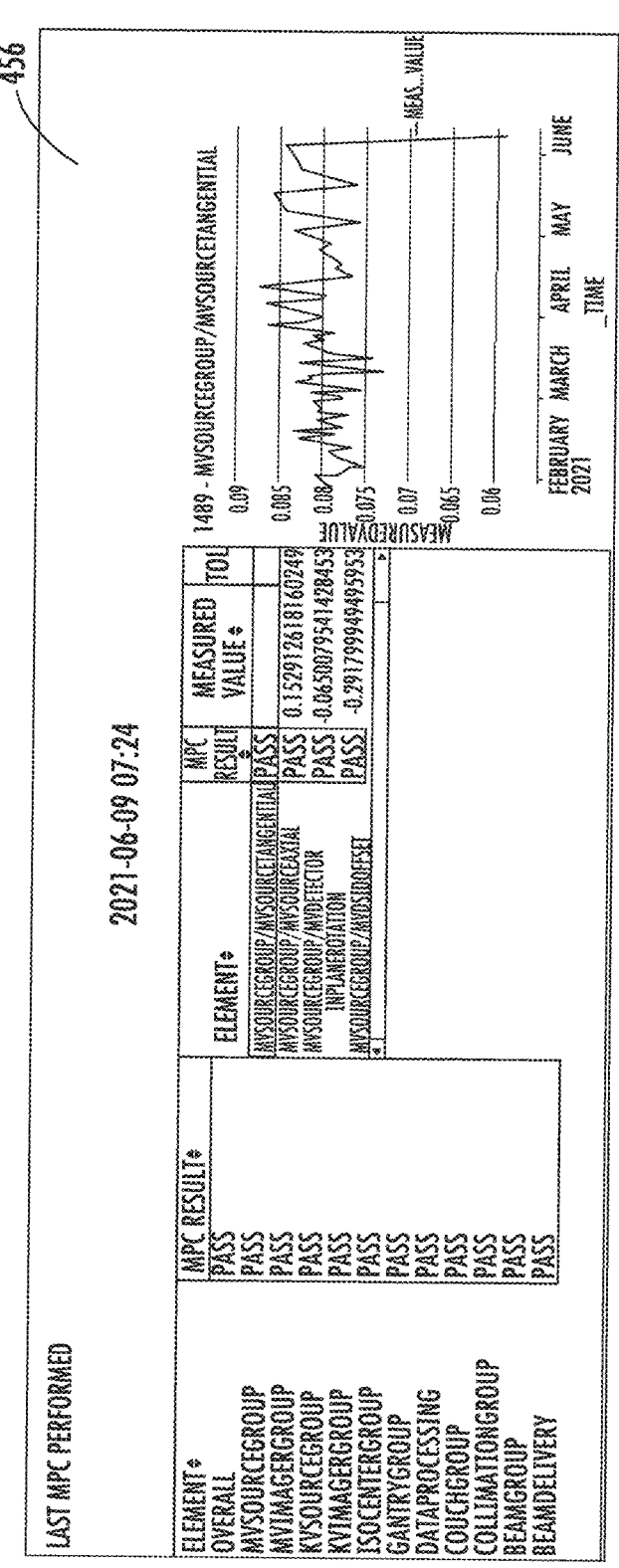
Figure 4Q:
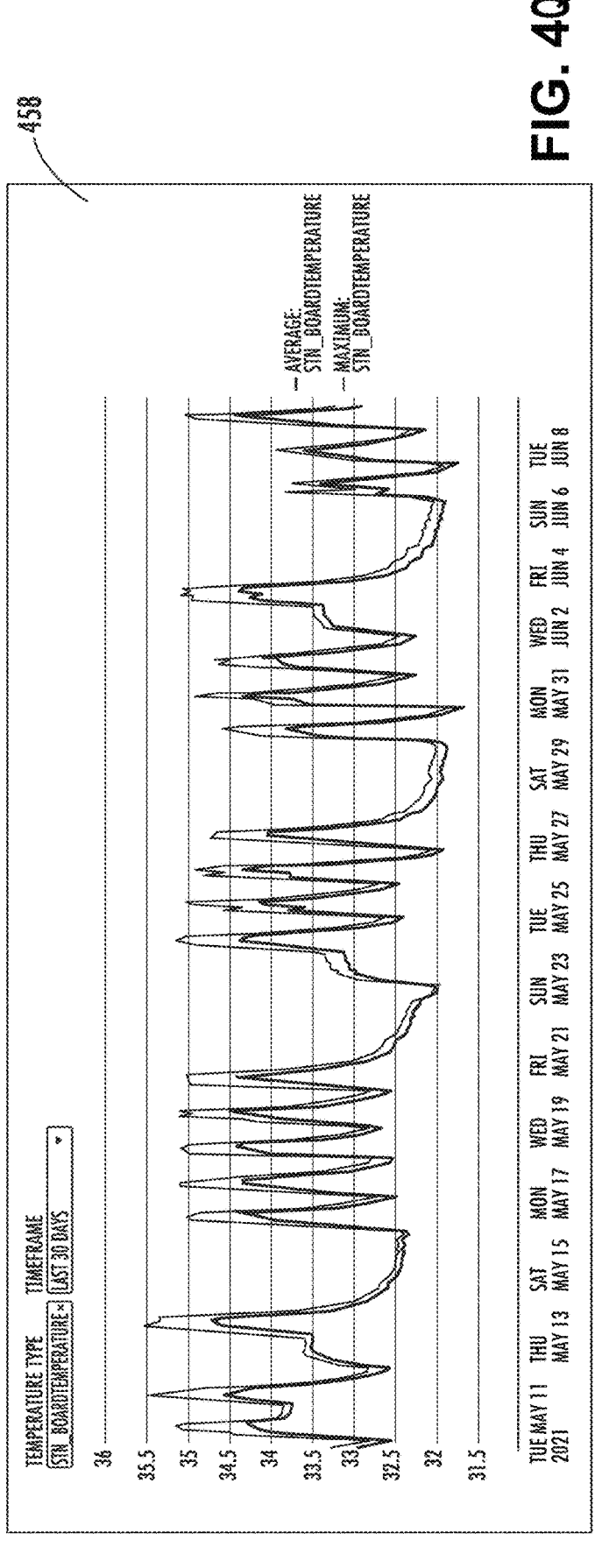

Referring to FIG. 4P, depicted is an example user interface 456 that depicts MPC trends. The user interface 456 can show MPC trends without requiring the user to download large files from the workstation of the medical device (e.g., the medical device computer 162, etc.). As shown in FIG. 4Q, the Machine Monitor can also include a tab that provides the user interface 458, which depicts an overview of the temperatures experienced by the medical device (e.g., gathered from one or more temperature sensors coupled to the medical device) in a graph of temperature over time.

Referring to FIG. 4R, depicted is an example user interface 460, which may be displayed via interaction with the "Version" tab in the Machine Monitor interface. The user interface 460 can list the version of all nodes and controllers of the identified medical device. Each entry in the list can include the current software version and/or the part number. The user interface 462 is a dashboard provides a comprehensive list of BGM parameters from all of the medical device worldwide. Information displayed in the user interface 462 can be useful for use in comparing parameters between medical devices that are close in PCSN (e.g., similar identifiers indicate similar manufacturing time). The dashboard shown in the user interface 462 may also be useful to BGM parameters for medical devices that are outliers.

FIG. 5 illustrates a flow diagram of a process executed in a system for processing information generated by radiotherapy machines, according to an embodiment. The method 500 may include steps 510-530. However, other embodiments may include additional or alternative steps, or may omit one or more steps altogether. The method 500 is described as being executed by a data processing system (e.g., a computer similar to the analytics server 110a, the data source 120, the end-user device 140, or the administrator computing device 150, described in FIG. 1). However, one or more steps of method 500 may be executed by any number of computing devices operating in the distributed computing system described in FIG. 1. For instance, one or more computing devices may locally perform part or all of the steps described in FIG. 5 or a cloud device may perform such steps.

At step 510, a data processing system (e.g., the analytics server 110a, the data source 120, the end-user device 140, or the administrator computing device 150) may generate a machine-readable object by executing an algorithm using an electronic log file. As described herein, radiotherapy machines (e.g., the medical devices 160) generate raw operational data, which can include electronic log files, during their operation. This information can include, for example, data relating to the patient (e.g., patient diagnosis, treatment status, etc.), data relating to the status of one or more components of the radiotherapy machine, information relating to passed or failed tests performed on the components of the radiotherapy machine, among any other information described herein. An electronic log file generated by a radiotherapy machine can include one or more operational attributes of the radiotherapy treatment performed on a patient, and may include a timestamp corresponding to when the treatment took place. Some non-limiting examples of operational attributes can include, for example, an orientation of at least one component of the radiotherapy machine (e.g., an angle of the chair on which the patient was positioned), an attribute of a radiation emitted by the radiation therapy machine (e.g., beam characteristic data, beam shape, beam direction, beam type, etc.), an amount of power (e.g., voltage, current) consumed by the radiotherapy machine, a number of cycles performed by one or more components of the radiotherapy machine.

Data analyzed by the data processing system is not limited to data generated during treatment of patients. Accordingly, operational attributes of radiotherapy machines can also be generated during other operations, for example, during quality assurance procedures performed on radiotherapy machines, during mock treatments executed at radiotherapy machines, during one or more testing procedures performed on radiotherapy machines, or during any other operation performed on or by radiotherapy machines. Another example of an operational attribute can be a number of workflow interruptions that occurred while operating the radiotherapy machine, for example, due to one or more faults at the radiotherapy machine.

As described herein above, the electronic log files generated by radiotherapy machines can be large and impracticable to analyze using conventional techniques. To manage this large amount of data, the data processing system can execute one or more algorithms over the electronic log files to generate machine-readable objects that are useable in further processes as described herein. To generate the machine-readable object, the data processing system may use one or more rule-based parsing algorithms, for example, to extract predetermined types of information according to the types of electronic log files generated by the radiotherapy machines. The data processing system can determine a type of an electronic log file (e.g., based on a file extension, a source of the file, or a header or other data in the electronic log file), and select a set of rules to apply to the log file to extract appropriate data. The data processing system may implement one or more pattern matching techniques, such as regular expression (regex) pattern matching techniques, to extract relevant information for the machine-readable objects from the electronic log files. The machine-readable objects can be data structures, such as JavaScript Object Notation (JSON) object files, or any other type of object-based data structure that can contain organized or structured information. The machine-readable objects can be stored, for example, as part of one or more data repositories, which may include non-relational databases such as NoSQL databases or other types of databases.

At step 520, the data processing system may execute a machine learning model (e.g., the machine learning model 111) using the generated machine-readable objects to predict one or more performance attributes of the radiotherapy machine. In a non-limiting example, the predicted performance attributes may indicate that the performance of one or more parts (e.g., mechanical or hardware components) of the radiotherapy that satisfies a threshold, such as a use or cycle threshold. For example, the threshold can indicate that a particular component of the radiotherapy machine has been overused or needs to be replaced. The data processing system can use machine learning models to generate indications of components of radiotherapy machines that have failed, are failing, or will fail within a predetermined time period. The predicted performance metric may indicate a remaining estimated time or a remaining number of treatments before a failure associated with the radiotherapy machine. Each radiotherapy machine (or the components thereof) may be rated for a predetermined number of cycles or operations. The machine learning models may be trained to generate an indication of how many cycles remain before a radiotherapy machine requires service, based on the machine readable objects generated by the data processing system.

The data processing system can train the machine learning models, for example, using a supervised training technique. The training data used to train the machine learning models may be gathered by accessing historic information generated by radiotherapy machines, and based on corresponding machine-readable objects of previously serviced radiotherapy machines. For example, when a maintenance worker services a radiotherapy machine, an electronic service record may be generated that indicates a particular fault that was serviced in the machine. This service record can serve as a "ground truth" for machine failure, which may be associated with raw operational information generated from the serviced radiotherapy machine prior to the service event or a detected failure event. This raw information may be converted into machine-readable objects using the processes described herein, and associated with the ground-truth failure information for the radiotherapy machine, which can operate as a label for training data. The labeled machine-readable objects generated from historic electronic log files can be used as training data by the data processing system when training the machine learning models. Other training processes are also possible, such as unsupervised training techniques or semi-supervised training techniques.

To generate a predicted performance attribute of a radiotherapy machine, the data processing system can input a set of machine-readable objects generated from raw data produced by the radiotherapy machine. The machine-readable objects can be selected based on the type of information included in the machine-readable objects. The data processing system may execute the machine learning models, for example, by propagating the input data through each layer of the models until an output value is generated. The outputs generated by the machine learning models may be, for example, a confidence score indicating a likelihood that the radiotherapy machine corresponds to a particular performance attribute (e.g., in need of preventative maintenance, is within a threshold of cycles before maintenance is required, is exhibiting or will likely exhibiting a predetermined fault, etc.). The machine learning models may be trained to output any type of attribute or characteristic of the radiotherapy machines described herein, using similar supervised training processes. The machine learning models may be trained to output an indication that there are one or more unperformed tasks associated with the radiotherapy machine.

The machine learning models may be trained to output an indication that the radiotherapy machine is in need of preventative maintenance. The data processing system can execute the machine learning models over the machine-readable objects of the radiotherapy machine to determine that the radiotherapy machine is due for preventative maintenance. The data processing system can determine that the radiotherapy machine is due for preventative maintenance based on the predicted performance metrics output by the machine learning models. For example, if the machine learning models output an indication that a radiotherapy machine is in need of maintenance within a predetermined number of cycles, the data processing system can determine that the radiotherapy machine is due for preventative maintenance to avoid potential faults. The outputs generated from executing the machine learning models described herein may be stored by the data processing system as machine-readable objects that are associated with the corresponding radiotherapy machine.

The data processing system may execute the machine learning models using the machine-readable objects in response to receiving a request from a user device (e.g., an end-user device 140, any other computing device described herein, etc.). For example, an end-user device may communicate with the data processing system via an automated chat bot executed by the data processing system, as described herein. The user can provide a request to the data processing system for a predicted performance attribute of a radiotherapy machine in a natural language. The data processing system can execute natural language processing techniques to process the query. The data processing system can retrieve one or more machine-readable objects corresponding to the radiotherapy machine identified from the query, and execute the machine learning models described herein over the machine-readable objects to generate the requested predicted performance attribute. The data processing system can then provide the predicted performance attribute in one or more messages via the automated chat bot, via a web-based interface, or via any of the user interfaces described herein. Any number, or any type, of machine-readable objects corresponding to a radiotherapy machine may be provided as input to the machine learning models to generate the predicted performance attributes or insights described herein.

At step 530, the data processing system may provide the predicted performance attribute of the radiotherapy machine to an electronic device. As described herein, the data processing system may provide an electronic platform, which may be accessed by an electronic device of a user. The user can interact with the data processing system by transmitting requests to the data processing system via the user interfaces of the electronic platform, and can receive predicted performance attributes of radiotherapy machines via the electronic platform. The data processing system may execute one or more steps of the method 500 in response to a request from a user that identifies a requested performance attribute of an identified radiotherapy machine, for example, generating a requested predicted performance attribute of an identified radiotherapy machine and displaying the predicted performance attribute at the electronic device in one or more user interfaces.

The data processing system may execute an automated chat bot, which may be integrated with natural language processing models. The data processing system can execute the natural language processing models over queries received by the user to generate machine-readable queries that identify, for example, one or more radiotherapy machines and a type of information requested about the radiotherapy machines. When executing the chat bot, the data processing system can instruct the electronic device to display an input element that receives a query in natural language. For example, the data processing system can provide one more user interfaces that can receive user input. The user interfaces may be displayed in a communication application executing on the electronic device of the user. The user interfaces may be displayed as part of a web-based interface provided by the data processing system to the electronic device. In addition to receiving queries via the automated chat bot, the data processing system can instruct the electronic device to display a graphical element representing the predicted performance attribute, for example, in one or more interfaces.

FIGS. 4A-4M show examples of user interfaces having predicted performance attributes, where the user interfaces provide insights into actionable data generated by radiotherapy machines. The data processing system can provide any type of information relating to the radiotherapy machines, as described herein, in one or more user interfaces to the electronic device. For example, the data processing system can present a user interface that displays one or more unperformed tasks associated with a radiotherapy machine. Each radiotherapy machine can be associated with a preventative maintenance plan. The information relating to whether the tasks preventative maintenance plan tasks have been completed can be stored in one or more machine-readable objects associated with the radiotherapy machine. The data processing system can identify one or more unperformed tasks associated with the radiotherapy machine by accessing the machine-readable objects associated with the radiotherapy machine, and can then display the one or more unperformed tasks in a user interface at the electronic device.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:
1. A method comprising:
receiving, by a processor, an electronic log file generated by a radiotherapy machine, the electronic log file comprising at least one operational attribute of the radiotherapy machine and a corresponding timestamp;
formatting, by the processor, the electronic log file into a machine-readable object having a structured format, the machine-readable object specifying a set of time-series multi-leaf collimator (MLC) values of the radiotherapy machine;
executing, by the processor, a machine learning model using the set of time-series MLC values of the machine-readable object to predict a performance attribute of the radiotherapy machine and at least one task that is to be performed with respect to the radiotherapy machine, the at least one task indicating a component of an MLC of the radiotherapy machine that is to be replaced;
providing, by the processor to an electronic device, a graphical user interface indicating the predicted performance attribute of the radiotherapy machine and the at least one task that is to be performed with respect to the radiotherapy machine;
identifying, by the processor, at least one service record indicating that the at least one task for the radiotherapy machine has been performed; and
storing, by the processor, an additional machine-readable object in association with the radiotherapy machine in response to the at least one service record indicating that the at least one task for the radiotherapy machine has been performed.
2. The method of claim 1, wherein providing the predicted performance attribute comprises:
instructing, by the processor, the electronic device to display an input element configured to receive a query in natural language; and
instructing, by the processor, the electronic device to display a graphical element representing the predicted performance attribute on the graphical user interface.
3. The method of claim 1, wherein the predicted performance attribute indicates an attribute of the component of the MLC of the radiotherapy machine that satisfies a threshold.
4. The method of claim 1, wherein the operational attribute comprises at least one of an orientation of at least one component of the radiotherapy machine, attribute of a radiation emitted by the radiotherapy machine, voltage consumed by the radiotherapy machine, a number of cycles operated by one or more components of the radiotherapy machine, or a number of workflow interruptions corresponding to the radiotherapy machine.
5. The method of claim 1, wherein the predicted performance attribute corresponds to a remaining estimated time or a remaining number of treatments before a failure associated with the radiotherapy machine.

6. The method of claim 1, further comprising training, by the processor, the machine learning model based on historical machine-readable objects and corresponding performance attributes.

7. The method of claim 6, further comprising generating, by the processor, the historical machine-readable objects and the corresponding predicted performance attributes based on a set of historical electronic documents and the service record of the radiotherapy machine.

8. The method of claim 1, further comprising determining, by the processor, that the radiotherapy machine is due for preventative maintenance based on the predicted performance attribute.

9. The method of claim 1, further comprising:

receiving, by the processor from the electronic device, an identifier of the radiotherapy machine via a natural language query; and retrieving, by the processor, the machine-readable object by accessing an electronic database using the identifier of the radiotherapy machine.

10. The method of claim 1, wherein the machine learning model is trained using a supervised learning technique.

11. A system comprising:

a processor configured to execute instructions stored on a non-transitory computer-readable medium to:

receive an electronic log file generated by a radiotherapy machine, the electronic log file comprising at least one operational attribute of the radiotherapy machine and a corresponding timestamp;

format the electronic log file into a machine-readable object having a structured format, the machine-readable object specifying a set of time-series multi-leaf collimator (MLC) values;

execute a machine learning model using the set of time-series MLC values of the machine-readable object to predict a performance attribute of the radiotherapy machine and at least one task that is to be performed with respect to the radiotherapy machine, the at least one task indicating a component of an MLC of the radiotherapy machine that is to be replaced;

provide a graphical user interface indicating the predicted performance attribute of the radiotherapy machine to an electronic device and the at least one task that is to be performed with respect to the radiotherapy machine;

identify at least one service record indicating that the at least one task for the radiotherapy machine has been performed; and store an additional machine-readable object in association with the radiotherapy machine in response to the at least one service record indicating that the at least one task for the radiotherapy machine has been performed.

12. The system of claim 11, wherein the non-transitory computer-readable medium contains instructions that when executed by the processor causes the processor to provide the predicted performance attribute by:

instructing the electronic device to display an input element configured to receive a query in natural language; and instructing the electronic device to display a graphical element representing the predicted performance attribute on the graphical user interface.

13. The system of claim 11, wherein the predicted performance attribute indicates an attribute of the component of the MLC of the radiotherapy machine that satisfies a threshold.

14. The system of claim 11, wherein the operational attribute comprises at least one of an orientation of at least one component of the radiotherapy machine, attribute of a radiation emitted by the radiotherapy machine, voltage consumed by the radiotherapy machine, a number of cycles operated by one or more components of the radiotherapy machine, or a number of workflow interruptions corresponding to the radiotherapy machine.

15. The system of claim 11, wherein the predicted performance attribute corresponds to a remaining estimated time or a remaining number of treatments before a failure associated with the radiotherapy machine.

16. The system of claim 11, wherein the non-transitory computer-readable medium contains instructions that when executed by the processor causes the processor to train the machine learning model based on historical machine-readable objects and corresponding performance attributes.

17. The system of claim 16, wherein the non-transitory computer-readable medium comprises instructions that, when executed by the processor, causes the processor to generate the historical machine-readable objects and the corresponding predicted performance attributes based on a set of historical electronic documents and the service record of the radiotherapy machine.

18. The system of claim 11, wherein the non-transitory computer-readable medium contains instructions that when executed by the processor causes the processor to determine that the radiotherapy machine is due for preventative maintenance based on the predicted performance attribute.

19. The system of claim 11, wherein the non-transitory computer-readable medium contains instructions that when executed by the processor causes the processor to:

receive, from the electronic device, an identifier of the radiotherapy machine via a natural language query; and retrieve the machine-readable object by accessing an electronic database using the identifier of the radiotherapy machine.

20. The system of claim 11, wherein the machine learning model is trained using a supervised learning technique.

* * * * *